(12) United States Patent
Williams et al.

(10) Patent No.: US 12,127,735 B2
(45) Date of Patent: *Oct. 29, 2024

(54) APPARATUS FOR ENDOSCOPIC PROCEDURES

(71) Applicant: Covidien LP, Mansfield, MA (US)

(72) Inventors: Justin Williams, Southbury, CT (US); Paul Scirica, Huntington, CT (US)

(73) Assignee: Covidien LP, Mansfield, MA (US)

( * ) Notice: Subject to any disclaimer, the term of this patent is extended or adjusted under 35 U.S.C. 154(b) by 440 days.

This patent is subject to a terminal disclaimer.

(21) Appl. No.: 17/510,578

(22) Filed: Oct. 26, 2021

(65) Prior Publication Data
US 2022/0039785 A1    Feb. 10, 2022

Related U.S. Application Data

(63) Continuation of application No. 16/421,682, filed on May 24, 2019, now Pat. No. 11,154,282, which is a
(Continued)

(51) Int. Cl.
*A61B 17/00*   (2006.01)
*A61B 17/072*  (2006.01)
*A61B 17/29*   (2006.01)

(52) U.S. Cl.
CPC .. *A61B 17/00234* (2013.01); *A61B 17/07207* (2013.01); *A61B 17/29* (2013.01);
(Continued)

(58) Field of Classification Search
CPC ............ A61B 17/00234; A61B 17/068; A61B 17/07207; A61B 17/115; A61B 17/1285;
(Continued)

(56) References Cited

U.S. PATENT DOCUMENTS 2,777,340 A    1/1957   Hettwer et al.
2,957,353 A    10/1960  Babacz
(Continued)

FOREIGN PATENT DOCUMENTS

AU    2008229795 A1    4/2009
CA       2451558 A1    1/2003
(Continued)

OTHER PUBLICATIONS

Extended European Search Report from Application No. EP 13175477.2 dated Feb. 6, 2014.
(Continued)

*Primary Examiner* — Robert A Lynch

(57) ABSTRACT

An electromechanical surgical device includes an end effector configured to perform at least one function, the end effector including an input drive axle projecting therefrom; and a shaft assembly. The shaft assembly includes a rotatable drive shaft; a proximal neck housing supported at a distal end of an outer tube; a distal neck housing pivotally connected to the proximal neck housing; a pivot pin interconnecting the proximal neck housing and the distal neck housing; and a gear train supported in the proximal neck housing, on the pivot pin, and in the distal neck housing. The gear train includes a proximal gear; an intermediate gear; a distal gear; and a pair of output gears, wherein each output gear defines a coupling socket each configured to selectively receive the drive axle of the end effector.

20 Claims, 18 Drawing Sheets

Related U.S. Application Data continuation of application No. 15/241,368, filed on Aug. 19, 2016, now Pat. No. 10,299,772, which is a continuation of application No. 13/769,419, filed on Feb. 18, 2013, now Pat. No. 9,421,003.

(52) U.S. Cl.
CPC ............... *A61B 2017/00398* (2013.01); *A61B 2017/0046* (2013.01); *A61B 2017/00473* (2013.01); *A61B 2017/00734* (2013.01); *A61B 2017/2903* (2013.01); *A61B 2017/2927* (2013.01); *A61B 2017/2931* (2013.01); *A61B 2017/2943* (2013.01)

(58) Field of Classification Search
CPC .......... A61B 17/29; A61B 2017/00398; A61B 2017/0046; A61B 2017/00473; A61B 2017/00477; A61B 2017/00734; A61B 2017/2901; A61B 2017/2903; A61B 2017/2927; A61B 2017/2931; A61B 2017/2943

See application file for complete search history.

(56) References Cited

U.S. PATENT DOCUMENTS

| | | |
|---|---|---|
| 3,111,328 A | 11/1963 | Di Rito et al. |
| 3,695,058 A | 10/1972 | Keith, Jr. |
| 3,734,515 A | 5/1973 | Dudek |
| 3,759,336 A | 9/1973 | Marcovitz et al. |
| 4,162,399 A | 7/1979 | Hudson |
| 4,606,343 A | 8/1986 | Conta et al. |
| 4,705,038 A | 11/1987 | Sjostrom et al. |
| 4,722,685 A | 2/1988 | de Estrada et al. |
| 4,823,807 A | 4/1989 | Russell et al. |
| 4,874,181 A | 10/1989 | Hsu |
| 5,129,118 A | 7/1992 | Walmesley |
| 5,129,570 A | 7/1992 | Schulze et al. |
| 5,152,744 A | 10/1992 | Krause et al. |
| 5,301,061 A | 4/1994 | Nakada et al. |
| 5,312,023 A | 5/1994 | Green et al. |
| 5,326,013 A | 7/1994 | Green et al. |
| 5,350,355 A | 9/1994 | Sklar |
| 5,383,874 A | 1/1995 | Jackson et al. |
| 5,383,880 A | 1/1995 | Hooven |
| 5,389,098 A | 2/1995 | Tsuruta et al. |
| 5,395,033 A | 3/1995 | Byrne et al. |
| 5,400,267 A | 3/1995 | Denen et al. |
| 5,411,508 A | 5/1995 | Bessler et al. |
| 5,413,267 A | 5/1995 | Solyntjes et al. |
| 5,427,087 A | 6/1995 | Ito et al. |
| 5,449,365 A * | 9/1995 | Green ............... A61B 17/1285 606/151 |
| 5,467,911 A | 11/1995 | Tsuruta et al. |
| 5,476,379 A | 12/1995 | Disel |
| 5,487,499 A | 1/1996 | Sorrentino et al. |
| 5,518,163 A | 5/1996 | Hooven |
| 5,518,164 A | 5/1996 | Hooven |
| 5,526,822 A | 6/1996 | Burbank et al. |
| 5,529,235 A | 6/1996 | Boiarski et al. |
| 5,535,934 A | 7/1996 | Boiarski et al. |
| 5,535,937 A | 7/1996 | Boiarski et al. |
| 5,540,375 A | 7/1996 | Bolanos et al. |
| 5,540,706 A | 7/1996 | Aust et al. |
| 5,542,594 A | 8/1996 | McKean et al. |
| 5,562,239 A | 10/1996 | Boiarski et al. |
| 5,632,432 A | 5/1997 | Schulze et al. |
| 5,653,374 A | 8/1997 | Young et al. |
| 5,658,300 A | 8/1997 | Bito et al. |
| 5,667,517 A | 9/1997 | Hooven |
| 5,693,042 A | 12/1997 | Boiarski et al. |
| 5,704,534 A | 1/1998 | Huitema et al. |
| 5,713,505 A | 2/1998 | Huitema |
| 5,762,603 A | 6/1998 | Thompson |
| 5,779,130 A | 7/1998 | Alesi et al. |
| 5,782,396 A | 7/1998 | Mastri et al. |
| 5,782,397 A | 7/1998 | Koukline |
| 5,820,009 A | 10/1998 | Melling et al. |
| 5,863,159 A | 1/1999 | Lasko |
| 5,865,361 A | 2/1999 | Milliman et al. |
| 5,908,427 A | 6/1999 | McKean et al. |
| 5,954,259 A | 9/1999 | Viola et al. |
| 5,964,774 A | 10/1999 | McKean et al. |
| 5,993,454 A | 11/1999 | Longo |
| 6,010,054 A | 1/2000 | Johnson et al. |
| 6,017,354 A | 1/2000 | Culp et al. |
| 6,032,849 A | 3/2000 | Mastri et al. |
| 6,045,560 A | 4/2000 | McKean et al. |
| 6,090,123 A | 7/2000 | Culp et al. |
| 6,126,651 A | 10/2000 | Mayer |
| 6,129,547 A | 10/2000 | Cise et al. |
| 6,239,732 B1 | 5/2001 | Cusey |
| 6,241,139 B1 | 6/2001 | Milliman et al. |
| 6,264,086 B1 | 7/2001 | McGuckin, Jr. |
| 6,264,087 B1 | 7/2001 | Whitman |
| 6,302,311 B1 | 10/2001 | Adams et al. |
| 6,315,184 B1 | 11/2001 | Whitman |
| 6,321,855 B1 | 11/2001 | Barnes |
| 6,329,778 B1 | 12/2001 | Culp et al. |
| 6,343,731 B1 | 2/2002 | Adams et al. |
| 6,348,061 B1 | 2/2002 | Whitman |
| 6,368,324 B1 | 4/2002 | Dinger et al. |
| 6,371,909 B1 | 4/2002 | Hoeg et al. |
| 6,434,507 B1 | 8/2002 | Clayton et al. |
| 6,443,973 B1 | 9/2002 | Whitman |
| 6,459,822 B1 | 10/2002 | Hathaway et al. |
| 6,461,372 B1 | 10/2002 | Jensen et al. |
| 6,471,637 B1 | 10/2002 | Green et al. |
| 6,488,197 B1 | 12/2002 | Whitman |
| 6,491,201 B1 | 12/2002 | Whitman |
| 6,533,157 B1 | 3/2003 | Whitman |
| 6,537,280 B2 | 3/2003 | Dinger et al. |
| 6,610,066 B2 | 8/2003 | Dinger et al. |
| 6,611,793 B1 | 8/2003 | Burnside et al. |
| 6,645,218 B1 | 11/2003 | Cassidy et al. |
| 6,654,999 B2 | 12/2003 | Stoddard et al. |
| 6,698,643 B2 | 3/2004 | Whitman |
| 6,699,177 B1 | 3/2004 | Wang et al. |
| 6,716,233 B1 | 4/2004 | Whitman |
| 6,783,533 B2 | 8/2004 | Green et al. |
| 6,792,390 B1 | 9/2004 | Burnside et al. |
| 6,793,652 B1 | 9/2004 | Whitman et al. |
| 6,817,508 B1 | 11/2004 | Racenet et al. |
| 6,830,174 B2 | 12/2004 | Hillstead et al. |
| 6,846,308 B2 | 1/2005 | Whitman et al. |
| 6,846,309 B2 | 1/2005 | Whitman et al. |
| 6,849,071 B2 | 2/2005 | Whitman et al. |
| 6,905,057 B2 | 6/2005 | Swayze et al. |
| 6,959,852 B2 | 11/2005 | Shelton, IV et al. |
| 6,964,363 B2 | 11/2005 | Wales et al. |
| 6,981,628 B2 | 1/2006 | Wales |
| 6,981,941 B2 | 1/2006 | Whitman et al. |
| 6,986,451 B1 | 1/2006 | Mastri et al. |
| 6,988,649 B2 | 1/2006 | Shelton, IV et al. |
| 7,032,798 B2 | 4/2006 | Whitman et al. |
| RE39,152 E | 6/2006 | Aust et al. |
| 7,055,731 B2 | 6/2006 | Shelton, IV et al. |
| 7,059,508 B2 | 6/2006 | Shelton, IV et al. |
| 7,077,856 B2 | 7/2006 | Whitman |
| 7,111,769 B2 | 9/2006 | Wales et al. |
| 7,122,029 B2 | 10/2006 | Koop et al. |
| 7,140,528 B2 | 11/2006 | Shelton, IV |
| 7,143,923 B2 | 12/2006 | Shelton, IV et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,172,104 B2 | 2/2007 | Scirica et al. |
| 7,225,964 B2 | 6/2007 | Mastri et al. |
| 7,238,021 B1 | 7/2007 | Johnson |
| 7,246,734 B2 | 7/2007 | Shelton, IV |
| 7,328,828 B2 | 2/2008 | Ortiz et al. |
| 7,364,061 B2 | 4/2008 | Swayze et al. |

(56) References Cited

U.S. PATENT DOCUMENTS

| | | |
|---|---|---|
| 7,380,695 B2 | 6/2008 | Doll et al. |
| 7,380,696 B2 | 6/2008 | Shelton, IV et al. |
| 7,404,508 B2 | 7/2008 | Smith et al. |
| 7,407,078 B2 | 8/2008 | Shelton, IV et al. |
| 7,416,101 B2 | 8/2008 | Shelton, IV et al. |
| 7,419,080 B2 | 9/2008 | Smith et al. |
| 7,422,139 B2 | 9/2008 | Shelton, IV et al. |
| 7,431,189 B2 | 10/2008 | Shelton, IV et al. |
| 7,441,684 B2 | 10/2008 | Shelton, IV et al. |
| 7,448,525 B2 | 11/2008 | Shelton, IV et al. |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,481,347 B2 | 1/2009 | Roy |
| 7,481,824 B2 | 1/2009 | Boudreaux et al. |
| 7,487,899 B2 | 2/2009 | Shelton, IV et al. |
| 7,549,564 B2 | 6/2009 | Boudreaux |
| 7,565,993 B2 | 7/2009 | Milliman et al. |
| 7,568,603 B2 | 8/2009 | Shelton, IV et al. |
| 7,575,144 B2 | 8/2009 | Ortiz et al. |
| 7,588,176 B2 | 9/2009 | Timm et al. |
| 7,637,409 B2 | 12/2009 | Marczyk |
| 7,641,093 B2 | 1/2010 | Doll et al. |
| 7,644,848 B2 | 1/2010 | Swayze et al. |
| 7,670,334 B2 | 3/2010 | Hueil et al. |
| 7,673,780 B2 | 3/2010 | Shelton, IV et al. |
| 7,699,835 B2 | 4/2010 | Lee et al. |
| 7,721,931 B2 | 5/2010 | Shelton, IV et al. |
| 7,740,159 B2 | 6/2010 | Shelton, IV et al. |
| 7,743,960 B2 | 6/2010 | Whitman et al. |
| 7,758,613 B2 | 7/2010 | Whitman |
| 7,766,210 B2 | 8/2010 | Shelton, IV et al. |
| 7,770,773 B2 | 8/2010 | Whitman et al. |
| 7,770,775 B2 | 8/2010 | Shelton, IV et al. |
| 7,793,812 B2 | 9/2010 | Moore et al. |
| 7,799,039 B2 | 9/2010 | Shelton, IV et al. |
| 7,802,712 B2 | 9/2010 | Milliman et al. |
| 7,822,458 B2 | 10/2010 | Webster, III et al. |
| 7,845,534 B2 | 12/2010 | Viola et al. |
| 7,845,537 B2 | 12/2010 | Shelton, IV et al. |
| 7,857,185 B2 | 12/2010 | Swayze et al. |
| 7,870,989 B2 | 1/2011 | Viola et al. |
| 7,905,897 B2 | 3/2011 | Whitman et al. |
| 7,918,230 B2 | 4/2011 | Whitman et al. |
| 7,922,719 B2 | 4/2011 | Ralph et al. |
| 7,947,034 B2 | 5/2011 | Whitman |
| 7,951,071 B2 | 5/2011 | Whitman et al. |
| 7,954,682 B2 | 6/2011 | Giordano et al. |
| 7,959,051 B2 | 6/2011 | Smith et al. |
| 7,963,433 B2 | 6/2011 | Whitman et al. |
| 7,967,178 B2 | 6/2011 | Scirica et al. |
| 7,967,179 B2 | 6/2011 | Olson et al. |
| 7,992,758 B2 | 8/2011 | Whitman et al. |
| 8,016,178 B2 | 9/2011 | Olson et al. |
| 8,016,855 B2 | 9/2011 | Whitman et al. |
| 8,020,743 B2 | 9/2011 | Shelton, IV |
| 8,025,199 B2 | 9/2011 | Whitman et al. |
| 8,052,024 B2 | 11/2011 | Viola et al. |
| 8,056,787 B2 | 11/2011 | Boudreaux et al. |
| 8,114,118 B2 | 2/2012 | Knodel et al. |
| 8,132,705 B2 | 3/2012 | Viola et al. |
| 8,152,516 B2 | 4/2012 | Harvey et al. |
| 8,157,150 B2 | 4/2012 | Viola et al. |
| 8,157,151 B2 | 4/2012 | Ingmanson et al. |
| 8,182,494 B1 | 5/2012 | Yencho et al. |
| 8,186,555 B2 | 5/2012 | Shelton, IV et al. |
| 8,186,587 B2 | 5/2012 | Zmood et al. |
| 8,220,367 B2 | 7/2012 | Hsu |
| 8,235,273 B2 | 8/2012 | Olson et al. |
| 8,241,322 B2 | 8/2012 | Whitman et al. |
| 8,272,554 B2 | 9/2012 | Whitman et al. |
| 8,292,150 B2 | 10/2012 | Bryant |
| 8,292,888 B2 | 10/2012 | Whitman |
| 8,303,581 B2 | 11/2012 | Arts et al. |
| 8,342,379 B2 | 1/2013 | Whitman et al. |
| 8,353,440 B2 | 1/2013 | Whitman et al. |
| 8,357,144 B2 | 1/2013 | Whitman et al. |
| 8,365,633 B2 | 2/2013 | Simaan et al. |
| 8,365,972 B2 | 2/2013 | Aranyi et al. |
| 8,371,492 B2 | 2/2013 | Aranyi et al. |
| 8,372,057 B2 | 2/2013 | Cude et al. |
| 8,391,957 B2 | 3/2013 | Carlson et al. |
| 8,424,739 B2 | 4/2013 | Racenet et al. |
| 8,454,585 B2 | 6/2013 | Whitman |
| 8,505,802 B2 | 8/2013 | Viola et al. |
| 8,517,241 B2 | 8/2013 | Nicholas et al. |
| 8,551,076 B2 | 10/2013 | Duval et al. |
| 8,561,871 B2 | 10/2013 | Rajappa et al. |
| 8,623,000 B2 | 1/2014 | Humayun et al. |
| 8,632,463 B2 | 1/2014 | Drinan et al. |
| 8,647,258 B2 | 2/2014 | Aranyi et al. |
| 8,657,174 B2 | 2/2014 | Yates et al. |
| 8,657,177 B2 | 2/2014 | Scirica et al. |
| 8,672,206 B2 | 3/2014 | Aranyi et al. |
| 8,696,552 B2 | 4/2014 | Whitman |
| 8,708,213 B2 | 4/2014 | Shelton, IV et al. |
| 8,752,749 B2 | 6/2014 | Moore et al. |
| 8,806,973 B2 | 8/2014 | Ross et al. |
| 8,851,355 B2 | 10/2014 | Aranyi et al. |
| 8,858,571 B2 | 10/2014 | Shelton, IV et al. |
| 8,967,443 B2 | 3/2015 | McCuen |
| 9,421,003 B2 * | 8/2016 | Williams ......... A61B 17/00234 |
| 10,299,772 B2 * | 5/2019 | Williams ............. A61B 17/29 |
| 11,154,282 B2 * | 10/2021 | Williams ......... A61B 17/07207 |
| 2003/0038938 A1 | 2/2003 | Jung et al. |
| 2003/0130677 A1 | 7/2003 | Whitman et al. |
| 2004/0111012 A1 | 6/2004 | Whitman |
| 2004/0133189 A1 | 7/2004 | Sakurai |
| 2004/0176751 A1 | 9/2004 | Weitzner et al. |
| 2005/0131442 A1 | 6/2005 | Yachia et al. |
| 2006/0142656 A1 | 6/2006 | Malackowski et al. |
| 2006/0278680 A1 | 12/2006 | Viola et al. |
| 2007/0023477 A1 | 2/2007 | Whitman et al. |
| 2007/0029363 A1 | 2/2007 | Popov |
| 2007/0055219 A1 | 3/2007 | Whitman et al. |
| 2007/0084897 A1 | 4/2007 | Shelton et al. |
| 2007/0102472 A1 | 5/2007 | Shelton |
| 2007/0152014 A1 | 7/2007 | Gillum et al. |
| 2007/0175949 A1 | 8/2007 | Shelton et al. |
| 2007/0175950 A1 | 8/2007 | Shelton et al. |
| 2007/0175951 A1 | 8/2007 | Shelton et al. |
| 2007/0175955 A1 | 8/2007 | Shelton et al. |
| 2007/0175961 A1 | 8/2007 | Shelton et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0058801 A1 | 3/2008 | Taylor et al. |
| 2008/0083808 A1 | 4/2008 | Scirica |
| 2008/0105730 A1 | 5/2008 | Racenet et al. |
| 2008/0109012 A1 | 5/2008 | Falco et al. |
| 2008/0110958 A1 | 5/2008 | McKenna et al. |
| 2008/0185419 A1 | 8/2008 | Smith et al. |
| 2008/0188841 A1 | 8/2008 | Tomasello et al. |
| 2008/0197167 A1 | 8/2008 | Viola et al. |
| 2008/0208195 A1 | 8/2008 | Shores et al. |
| 2008/0251561 A1 | 10/2008 | Eades et al. |
| 2008/0255413 A1 | 10/2008 | Zemlok et al. |
| 2008/0255607 A1 | 10/2008 | Zemlok |
| 2008/0262654 A1 | 10/2008 | Omori et al. |
| 2008/0308603 A1 | 12/2008 | Shelton et al. |
| 2009/0090763 A1 | 4/2009 | Zemlok et al. |
| 2009/0099876 A1 | 4/2009 | Whitman |
| 2009/0101629 A1 | 4/2009 | Adams |
| 2009/0101692 A1 | 4/2009 | Whitman et al. |
| 2009/0138006 A1 | 5/2009 | Bales et al. |
| 2009/0145947 A1 | 6/2009 | Scirica et al. |
| 2009/0171147 A1 | 7/2009 | Lee et al. |
| 2009/0179063 A1 | 7/2009 | Milliman et al. |
| 2009/0182193 A1 | 7/2009 | Whitman et al. |
| 2009/0209990 A1 | 8/2009 | Yates et al. |
| 2009/0254094 A1 | 10/2009 | Knapp et al. |
| 2010/0069942 A1 | 3/2010 | Shelton, IV |
| 2010/0225073 A1 | 9/2010 | Porter et al. |

(56) References Cited

U.S. PATENT DOCUMENTS

| | | |
|---|---|---|
| 2011/0006101 A1 | 1/2011 | Hall et al. |
| 2011/0017801 A1 | 1/2011 | Zemlok et al. |
| 2011/0077673 A1 | 3/2011 | Grubac et al. |
| 2011/0108605 A1* | 5/2011 | Sapienza ......... A61B 17/07207 227/180.1 |
| 2011/0121049 A1 | 5/2011 | Malinouskas et al. |
| 2011/0125138 A1 | 5/2011 | Malinouskas et al. |
| 2011/0139851 A1 | 6/2011 | McCuen |
| 2011/0155783 A1 | 6/2011 | Rajappa et al. |
| 2011/0174099 A1 | 7/2011 | Ross et al. |
| 2011/0204119 A1 | 8/2011 | McCuen |
| 2011/0218522 A1 | 9/2011 | Whitman |
| 2011/0253765 A1 | 10/2011 | Nicholas et al. |
| 2011/0290854 A1 | 12/2011 | Timm et al. |
| 2011/0295242 A1 | 12/2011 | Spivey et al. |
| 2011/0295269 A1 | 12/2011 | Swensgard et al. |
| 2012/0000962 A1 | 1/2012 | Racenet et al. |
| 2012/0089131 A1 | 4/2012 | Zemlok et al. |
| 2012/0143002 A1 | 6/2012 | Aranyi et al. |
| 2012/0172924 A1 | 7/2012 | Allen, IV |
| 2012/0223121 A1 | 9/2012 | Viola et al. |
| 2012/0253329 A1 | 10/2012 | Zemlok et al. |
| 2012/0310220 A1 | 12/2012 | Malkowski et al. |
| 2012/0323226 A1 | 12/2012 | Chowaniec et al. |
| 2013/0018361 A1 | 1/2013 | Bryant |
| 2013/0098966 A1 | 4/2013 | Kostrzewski et al. |
| 2013/0098968 A1 | 4/2013 | Aranyi et al. |
| 2013/0098969 A1 | 4/2013 | Scirica et al. |
| 2013/0214025 A1 | 8/2013 | Zemlok et al. |
| 2013/0240596 A1 | 9/2013 | Whitman |
| 2013/0274722 A1 | 10/2013 | Kostrzewski et al. |
| 2013/0282052 A1 | 10/2013 | Aranyi et al. |
| 2013/0292451 A1 | 11/2013 | Viola et al. |
| 2013/0313304 A1 | 11/2013 | Shelton, IV et al. |
| 2013/0317486 A1 | 11/2013 | Nicholas et al. |
| 2013/0319706 A1 | 12/2013 | Nicholas et al. |
| 2013/0324978 A1 | 12/2013 | Nicholas et al. |
| 2013/0324979 A1 | 12/2013 | Nicholas et al. |
| 2013/0334281 A1 | 12/2013 | Williams |
| 2014/0012236 A1 | 1/2014 | Williams et al. |
| 2014/0012237 A1 | 1/2014 | Pribanic et al. |
| 2014/0012289 A1 | 1/2014 | Snow et al. |
| 2014/0025046 A1 | 1/2014 | Williams et al. |
| 2014/0110455 A1 | 4/2014 | Ingmanson et al. |
| 2014/0207182 A1 | 7/2014 | Zergiebel et al. |
| 2014/0236173 A1 | 8/2014 | Scirica et al. |
| 2014/0236174 A1 | 8/2014 | Williams et al. |
| 2014/0276932 A1 | 9/2014 | Williams et al. |
| 2014/0299647 A1 | 10/2014 | Scirica et al. |
| 2014/0303668 A1 | 10/2014 | Nicholas et al. |
| 2014/0358129 A1 | 12/2014 | Zergiebel et al. |
| 2014/0361068 A1 | 12/2014 | Aranyi et al. |
| 2014/0373652 A1 | 12/2014 | Zergiebel et al. |
| 2015/0048144 A1 | 2/2015 | Whitman |
| 2015/0076205 A1 | 3/2015 | Zergiebel |
| 2015/0080912 A1 | 3/2015 | Sapre |

FOREIGN PATENT DOCUMENTS

| | | | |
|---|---|---|---|
| CN | 101856251 A | | 10/2010 |
| CN | 102247182 A | | 11/2011 |
| DE | 102008053842 A1 | | 5/2010 |
| EP | 0634144 A1 | | 1/1995 |
| EP | 0648476 A1 | | 4/1995 |
| EP | 0686374 A2 | | 12/1995 |
| EP | 0705571 A1 | | 4/1996 |
| EP | 1563794 A1 | | 8/2005 |
| EP | 1690502 A1 | | 8/2006 |
| EP | 1723913 A1 | | 11/2006 |
| EP | 1736112 A1 | | 12/2006 |
| EP | 1759652 A2 | | 3/2007 |
| EP | 1769754 A1 | | 4/2007 |
| EP | 1772105 A1 | | 4/2007 |
| EP | 1813199 A1 | | 8/2007 |
| EP | 1813203 A2 | | 8/2007 |
| EP | 1813211 A2 | | 8/2007 |
| EP | 1908412 A2 | | 4/2008 |
| EP | 1917929 A1 | | 5/2008 |
| EP | 1943954 A2 | | 7/2008 |
| EP | 1943956 A2 | | 7/2008 |
| EP | 1943958 A1 | | 7/2008 |
| EP | 1943976 A2 | | 7/2008 |
| EP | 1952769 A2 | | 8/2008 |
| EP | 2005898 A2 | | 12/2008 |
| EP | 2027819 A1 | | 2/2009 |
| EP | 2044888 A2 | | 4/2009 |
| EP | 2044890 A1 | | 4/2009 |
| EP | 2055243 A2 | | 5/2009 |
| EP | 2090247 A1 | | 8/2009 |
| EP | 2098170 A2 | | 9/2009 |
| EP | 2100561 A2 | | 9/2009 |
| EP | 2100562 A2 | | 9/2009 |
| EP | 2165664 A2 | | 3/2010 |
| EP | 2236098 A2 | | 10/2010 |
| EP | 2245994 A1 | | 11/2010 |
| EP | 2263568 A2 | | 12/2010 |
| EP | 2272443 A1 | | 1/2011 |
| EP | 2316345 A1 | | 5/2011 |
| EP | 2324776 A2 | | 5/2011 |
| EP | 2329773 A1 | | 6/2011 |
| EP | 2333509 A1 | | 6/2011 |
| EP | 2377472 A1 | | 10/2011 |
| EP | 2462878 A1 | | 6/2012 |
| EP | 2462880 A2 | | 6/2012 |
| EP | 2462880 B1 | | 6/2012 |
| EP | 2491872 A1 | | 8/2012 |
| EP | 2586382 A2 | | 5/2013 |
| EP | 2606834 A2 | | 6/2013 |
| EP | 2676615 A2 | | 12/2013 |
| EP | 2815705 A1 | | 12/2014 |
| ES | 2333509 A1 | | 2/2010 |
| FR | 2861574 A1 | | 5/2005 |
| JP | 08038488 | | 2/1996 |
| JP | 2005125075 A | | 5/2005 |
| JP | 2005253632 A | | 9/2005 |
| JP | 2008036431 A | | 2/2008 |
| JP | 2009213903 A | | 9/2009 |
| WO | 9915086 A1 | | 4/1999 |
| WO | 0072760 A1 | | 12/2000 |
| WO | 0072765 A1 | | 12/2000 |
| WO | 03000138 A2 | | 1/2003 |
| WO | 03026511 A1 | | 4/2003 |
| WO | 03030743 A2 | | 4/2003 |
| WO | 03065916 A1 | | 8/2003 |
| WO | 03077769 A1 | | 9/2003 |
| WO | 03090630 A2 | | 11/2003 |
| WO | 2004107989 A1 | | 12/2004 |
| WO | 2004112618 A2 | | 12/2004 |
| WO | 2006042210 A2 | | 4/2006 |
| WO | 2007016290 A2 | | 2/2007 |
| WO | 2007026354 A1 | | 3/2007 |
| WO | 2007137304 A2 | | 11/2007 |
| WO | 2008131362 A2 | | 10/2008 |
| WO | 2008133956 A2 | | 11/2008 |
| WO | 2009/039510 A1 | | 3/2009 |
| WO | 2009039506 A1 | | 3/2009 |
| WO | 2007014355 A3 | | 4/2009 |
| WO | 2009132359 A2 | | 10/2009 |
| WO | 2009143092 A1 | | 11/2009 |
| WO | 2009149234 A1 | | 12/2009 |
| WO | 2011/090291 A2 | | 7/2011 |
| WO | 2011108840 A2 | | 9/2011 |
| WO | 2012040984 A1 | | 4/2012 |

OTHER PUBLICATIONS

Extended European Search Report from Application No. EP 13169998.5 dated Feb. 24, 2014.

Extended European Search Report corresponding to EP 13176805.3, dated Nov. 4, 2013.

Extended European Search Report from Application No. EP 13171742.3 dated Jan. 3, 2014.

(56) References Cited

OTHER PUBLICATIONS

Extended European Search Report from Application No. EP 14155339.6 dated Jul. 8, 2015.
European Search Report dated Mar. 10, 2017 issued in corresponding EP Application No. 16196533.0-1664.
Chinese Office Action dated Mar. 7, 2017 issued in corresponding Chinese Application No. 2014100552204.
Australian Examination Report dated Jun. 13, 2017 issued in corresponding Australian Application No. 2014200224.
Chinese Office Action dated Aug. 9, 2017 issued in corresponding Chinese Application No. 2014100552204.
Japanese Notice of Allowance dated Feb. 9, 2018 issued in corresponding Japanese Application No. 2014-027260. (Summary Form only).
Japanese Office Action dated Oct. 27, 2017 issued in corresponding Japanese Appln. No. 2014-027260.
Extended European Search Report corresponding to EP No. 11 17 8021.9, dated Jun. 4, 2013; (3 pp).
Extended European Search Report corresponding to EP No. 13 16 30317, completed Jun. 27, 2013 and dated Jul. 15, 2013; (8 pp).
Extended European Search Report corresponding to EP No. 12 18 6177.7, completed Aug. 14, 2013 and dated Aug. 23, 2013; (8 pp).
Partial European Search Report corresponding to EP No. 13 17 1742.3, completed Sep. 17, 2013 and dated Sep. 25, 2013; (8 pp).
Partial European Search Report corresponding to EP No. 13 17 2400.7, completed Sep. 18, 2013 and dated Oct. 1, 2013; (7 pp).
Extended European Search Report corresponding to EP No. 13 17 5475.6, completed Sep. 23, 2013 and dated Oct. 1, 2013; (8 pp).
Extended European Search Report corresponding to EP No. 13 17 5478.0, completed Sep. 24, 2013 and dated Oct. 2, 2013; (6 pp).
Extended European Search Report corresponding to EP No. 13 17 5479.8, completed Sep. 27, 2013 and dated Oct. 10, 2013; (7 pp).
Partial Extended European Search Report corresponding to EP 13 17 5477.2, completed Oct. 7, 2013 and dated Oct. 15, 2013; (7 pp).
Extended European Search Report corresponding to EP No. 08 25 2703.7, completed Oct. 23, 2008 and dated Oct. 31, 2008; (7 pp).
European Search Report corresponding to EP 10 25 2037.6; completed Mar. 1, 2011 and dated Mar. 9, 2011; 3 pages.
European Search Report corresponding to EP 10 25 2037.6; completed Mar. 1, 2011 and dated Mar. 9, 2011; 3 pp.
Japanese Office Action dated Oct. 27, 2017 issued in corresponding Japanese Appin. No. 2014-027260.
Japanese Notice of Allowance dated Feb. 9, 2018 issued in corresponding Japanese Application No. 2014-027260.
Extended European Search Report corresponding to EP No. 13 16 3033.7, completed Jun. 27, 2013 and dated Jul. 15. 2013; (8 pp).
International Search Report corresponding to PCT/US2005/027266, completed May 30, 2008 and dated Jun. 18, 2008; (2 pp.).
Extended European Search Report corresponding to EP 08 25 2703.7, completed Oct. 23, 2008 and dated Oct. 31, 2008; (7 pp.).
Extended European Search Report corresponding to EP 08 25 3184.9, completed Feb. 12, 2009 and dated Feb. 27, 2009; (3 pp.).
Extended European Search Report corresponding to EP 10 25 0228.3, completed May 20, 2010 and dated Jun. 1, 2010; (6 pp.).
Extended European Search Report corresponding to EP 10 25 205b437.6, completed Mar. 1, 2011 and dated Mar. 9, 2011; (3 pp.).
Extended European Search Report corresponding to EP 10 25 1968.3, completed on Jul. 4, 2011 and dated Jul. 14, 2011; (12 pp.).
Extended European Search Report corresponding to EP 11 15 2266.0, completed Jul. 15, 2011 and dated Jul. 28, 2011; (3 pp.).
Extended European Search Report corresponding to EP 11 25 0462.6, completed Jul. 20, 2011 and dated Jul. 28, 2011; (6 pp.).
Extended European Search Report corresponding to EP 11 25 0771.0, completed Feb. 7, 2012 and dated Feb. 17, 2012; (3 pp.).
Extended European Search Report corresponding to EP 06 78 8914.7, completed May 3, 2012 and dated May 11, 2012; (8 pp.).
Partial European Search Report corresponding to EP 12 18 6177.7, completed Jan. 30, 2013 and dated Feb. 12, 2013; (6 pp.).
Extended European Search Report from Application No. EP 13177163.6 dated Feb. 6, 2014.
European Search Report dated Mar. 10, 2017 issued in corresponding EP Application No. 161965310-1664.
Japanese Notice of Allowance dated Feb. 9, 2018 issued in corresponding Japanese Application No. 2014-027260. (Summary Form 144 only).
European Search Report corresponding to EP 10 25 2037.6; completed Mar. 1, 2011 and dated Mar. 9, 2011; 3 pp.
Extended European Search Report corresponding to EP No. 11 17 8021.9, mailed Jun. 4, 2013; (3 pp).
Extended European Search Report corresponding to EP No. 13 16 30317, completed Jun. 27, 2013 and mailed Jul. 15, 2013; (8 pp).
Extended European Search Report corresponding to EP No. 12 18 6177.7, completed Aug. 14, 2013 and mailed Aug. 23, 2013; (8 pp).
Partial European Search Report corresponding to EP No. 13 17 1742.3, completed Sep. 17, 2013 and mailed Sep. 25, 2013; (8 pp).
Partial European Search Report corresponding to EP No. 13 17 2400.7, completed Sep. 18, 2013 and mailed Oct. 1, 2013; (7 pp).
Extended European Search Report corresponding to EP No. 13 17 5475.6, completed Sep. 23, 2013 and mailed Oct. 1, 2013; (8 pp).
Extended European Search Report corresponding to EP No. 13 17 5478.0, completed Sep. 24, 2013 and mailed Oct. 2, 2013; (6 pp).
Extended European Search Report corresponding to EP No. 13 17 5479.8, completed Sep. 27, 2013 and mailed Oct. 10, 2013; (7 pp).
Partial Extended European Search Report corresponding to EP 13 17 5477.2, completed Oct. 7, 2013 and mailed Oct. 15, 2013; (7 pp).
Extended European Search Report corresponding to EP No. 08 25 2703.7, completed Oct. 23, 2008 and mailed Oct. 31, 2008; (7 pp).
European Search Report corresponding to EP 10 25 2037.6; completed Mar. 1, 2011 and mailed Mar. 9, 2011; 3 pages.
European search Report from Appl. No. 13177163.6 dated Nov. 15, 2013. (8 pp).
Extended European Search Report from EP Application No. 13172400.7 dated Jan. 21, 2014.
Extended European Search Report from EP Application No. 13189026.1 dated Jan. 31, 2014.
The extended European Search Report from Application No. EP 13177163.6 dated Feb. 6, 2014.
Extended European Search Report corresponding to EP No. 13 16 3033.7, completed Jun. 27, 2013 and mailed Jul. 15, 2013; (8 pp).
International Search Report corresponding to PCT/US2005/027266, completed May 30, 2008 and mailed Jun. 18, 2008; (2 pp.).
Extended European Search Report corresponding to EP 08 25 2703.7, completed Oct. 23, 2008 and mailed Oct. 31, 2008; (7 pp.).
Extended European Search Report corresponding to EP 08 25 3184.9, completed Feb. 12, 2009 and mailed Feb. 27, 2009; (3 pp.).
Extended European Search Report corresponding to EP 10 25 0228.3, completed May 20, 2010 and mailed Jun. 1, 2010; (6 pp.).
Extended European Search Report corresponding to EP 10 25 2037.6, completed Mar. 1, 2011 and mailed Mar. 9, 2011; (3 pp.).
Extended European Search Report corresponding to EP 10 25 1968.3, completed on Jul. 4, 2011 and mailed Jul. 14, 2011; (12 pp.).
Extended European Search Report corresponding to EP 11 15 2266.0, completed Jul. 15, 2011 and mailed Jul. 28, 2011; (3 pp.).
Extended European Search Report corresponding to EP 11 25 0462.6, completed Jul. 20, 2011 and mailed Jul. 28, 2011; (6 pp.).
Extended European Search Report corresponding to EP 11 25 0771.0, completed Feb. 7, 2012 and mailed Feb. 17, 2012; (3 pp.).
Extended European Search Report corresponding to EP 06 78 8914.7, completed May 3, 2012 and mailed May 11, 2012; (8 pp.).
Partial European Search Report corresponding to EP 12 18 6177.7, completed Jan. 30, 2013 and mailed Feb. 12, 2013; (6 pp.).

* cited by examiner

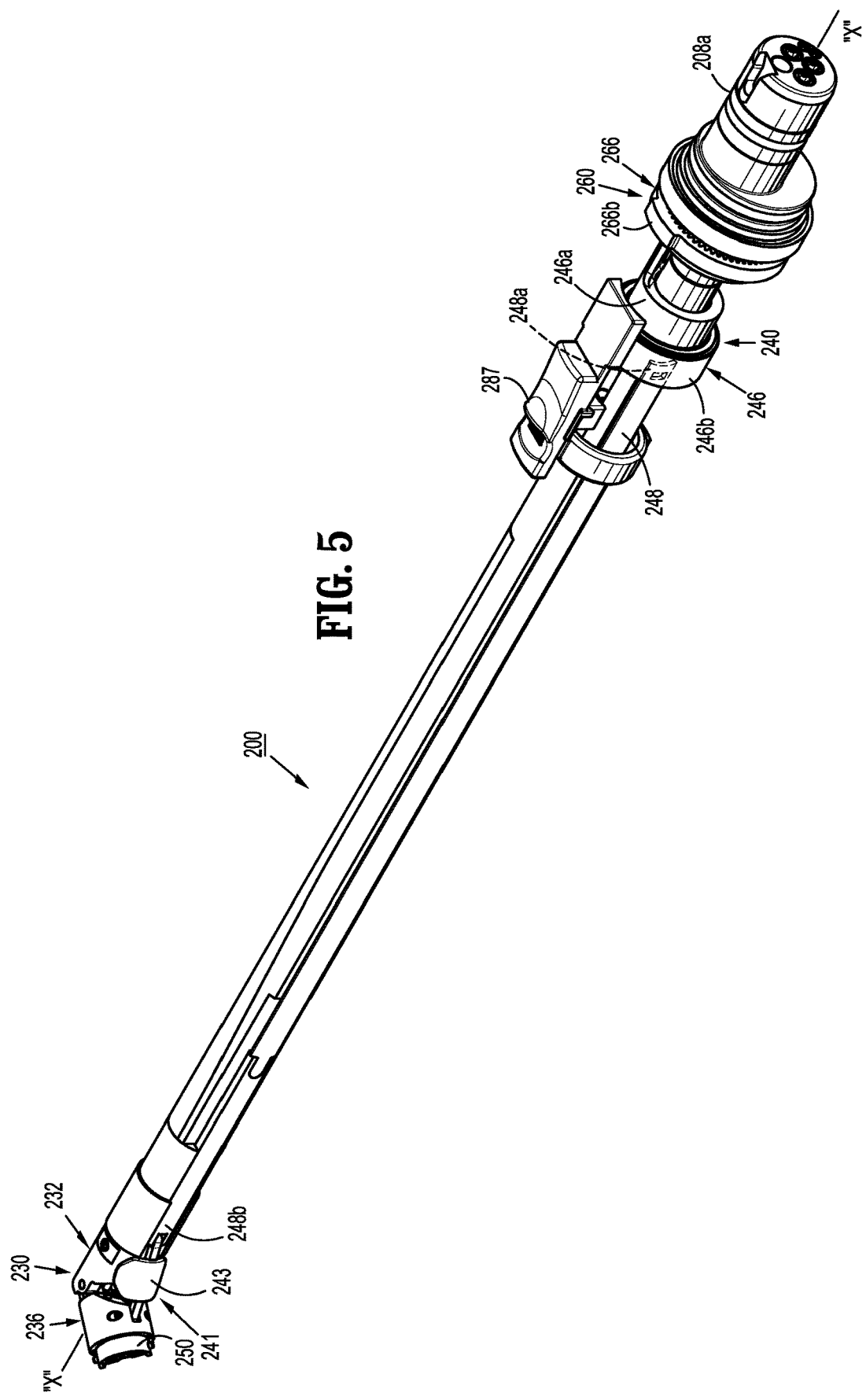

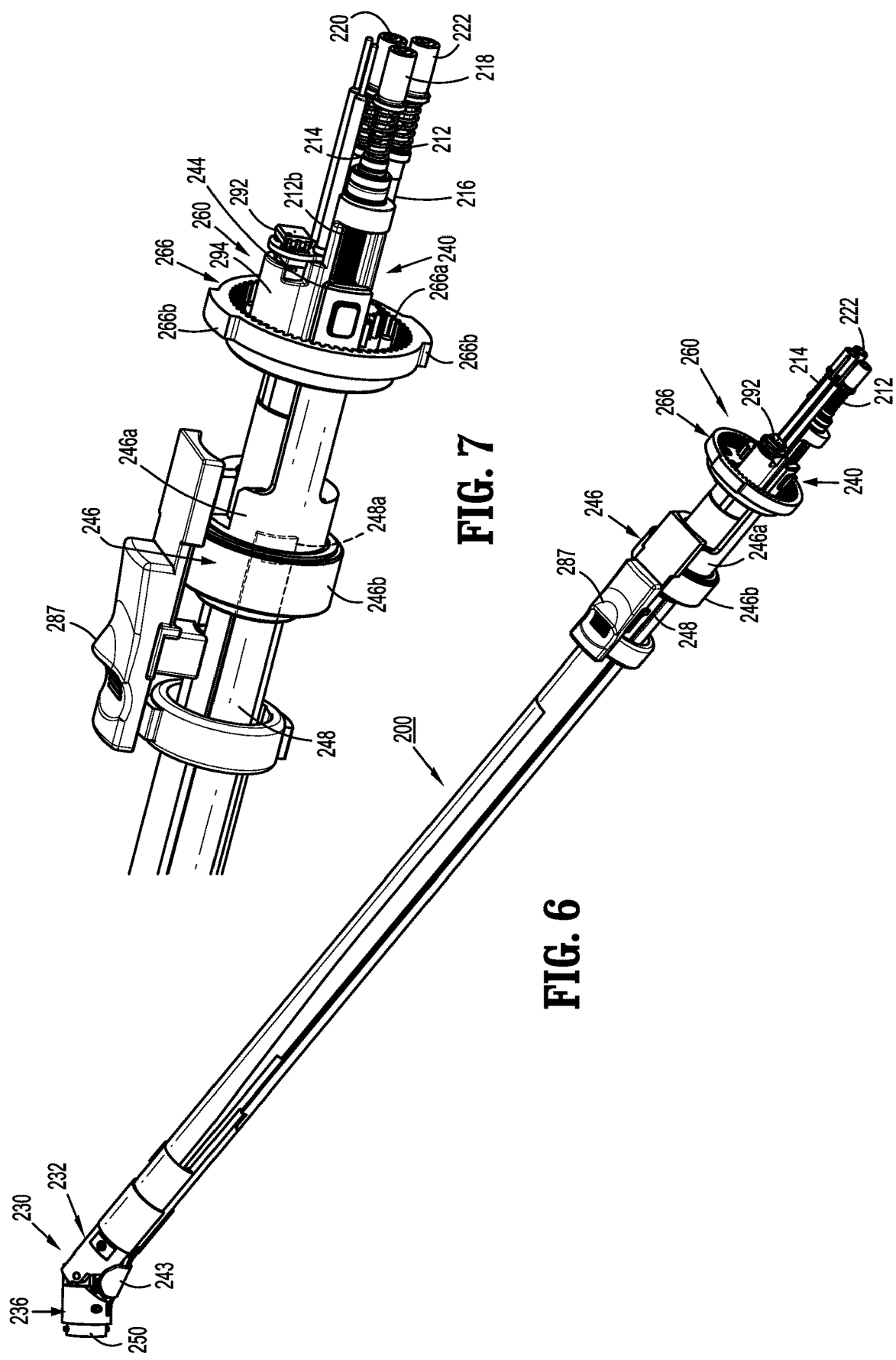

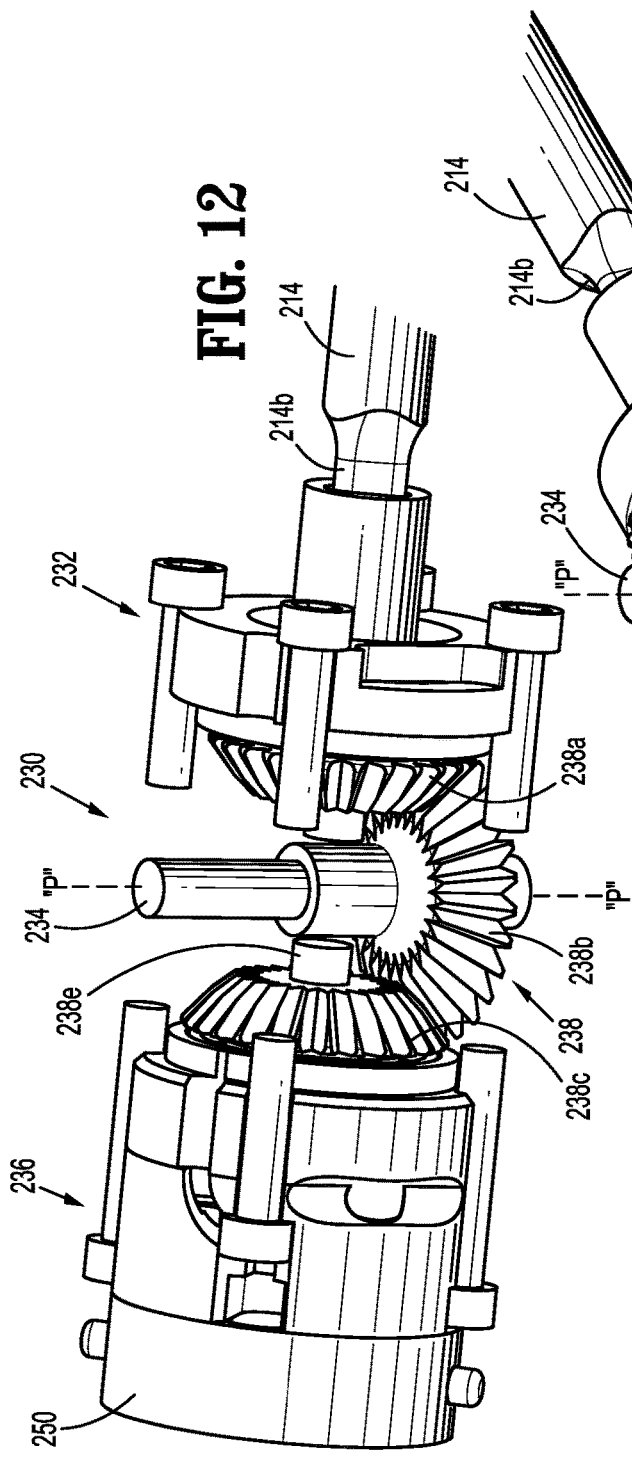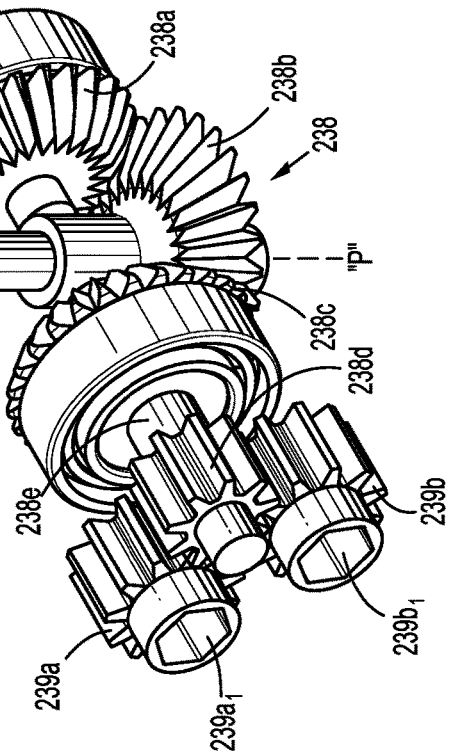

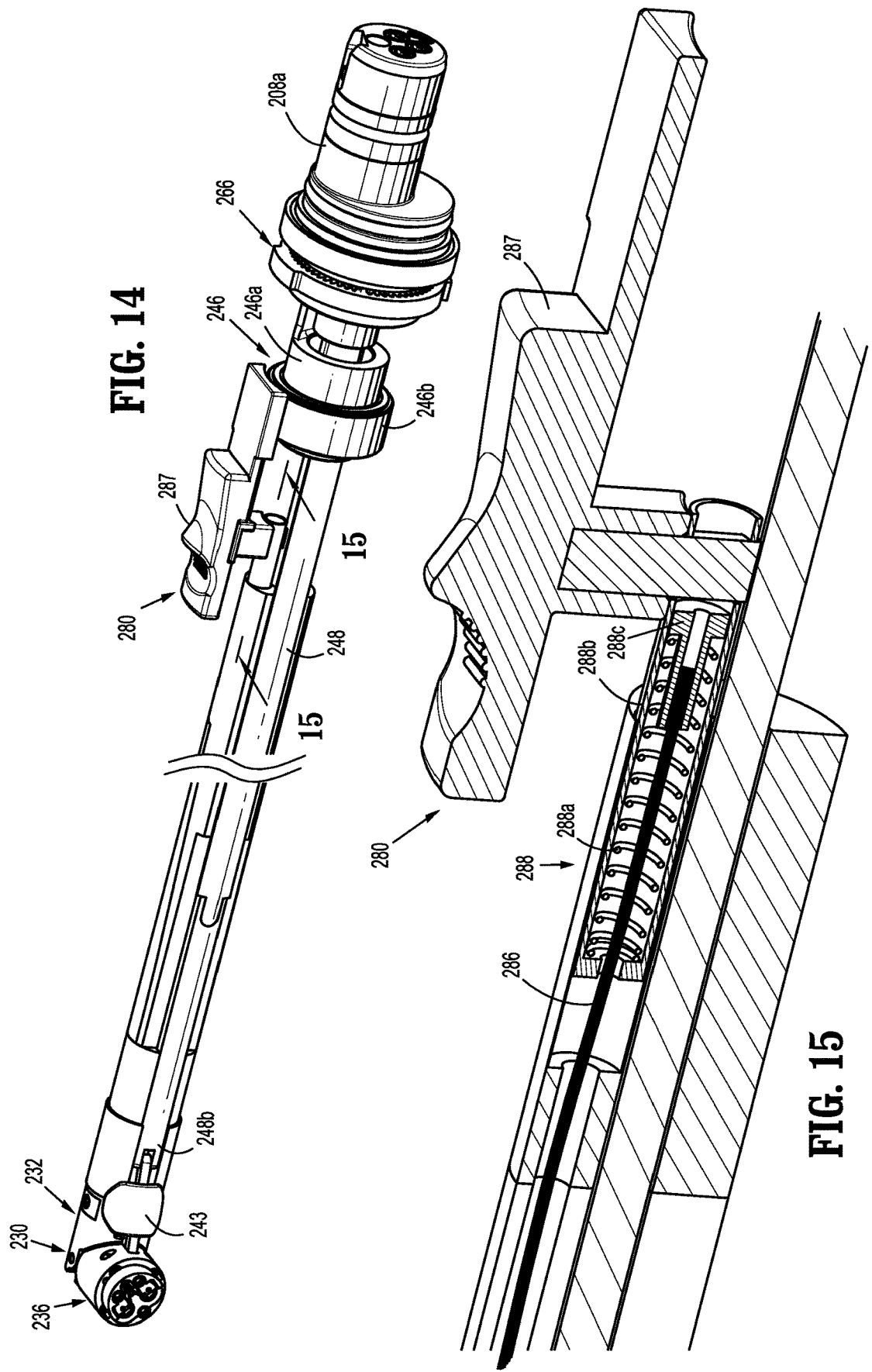

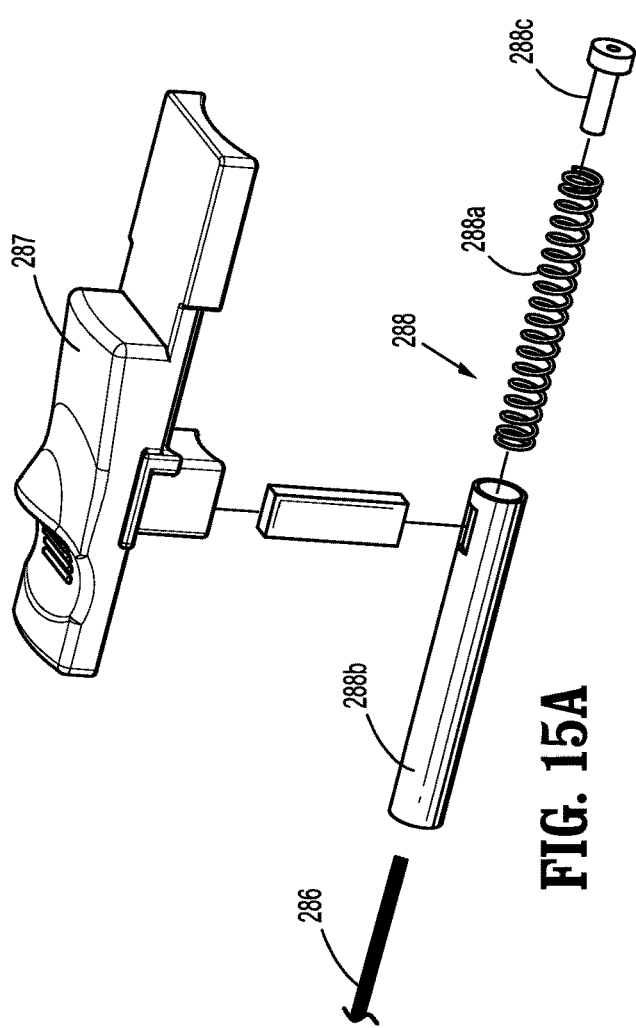
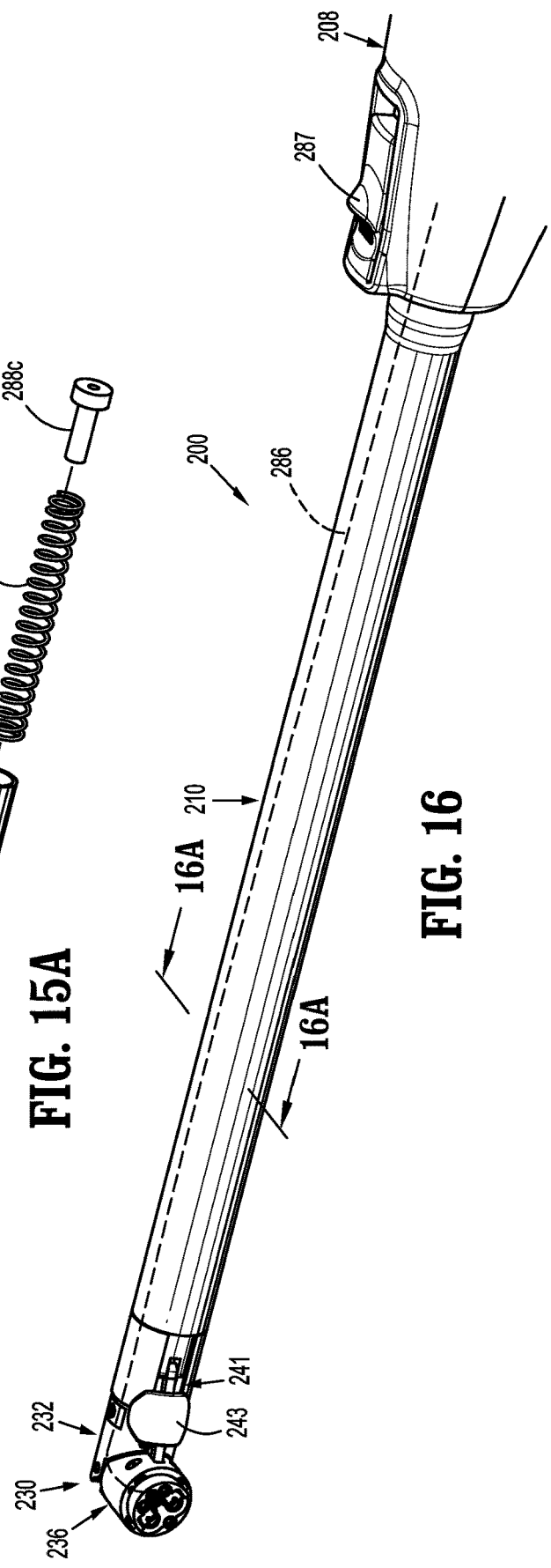
FIG. 15A
FIG. 16

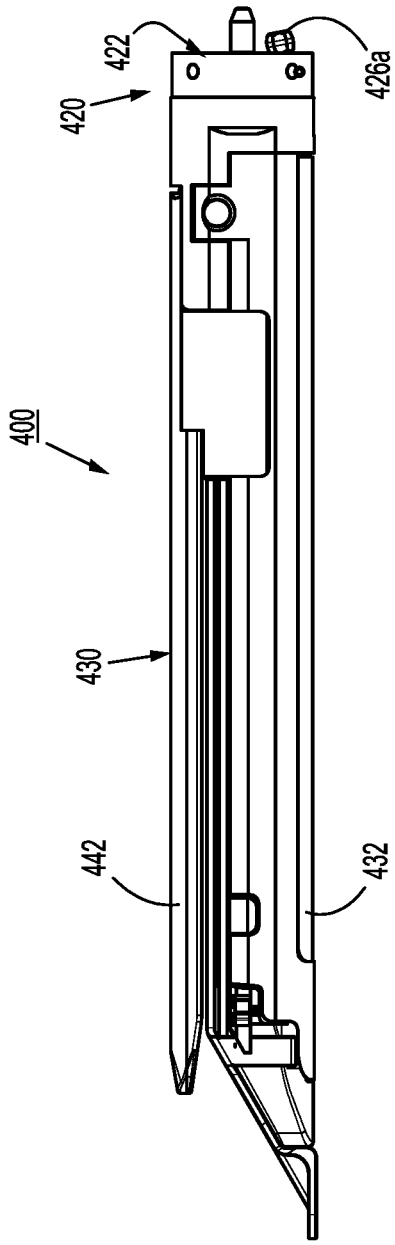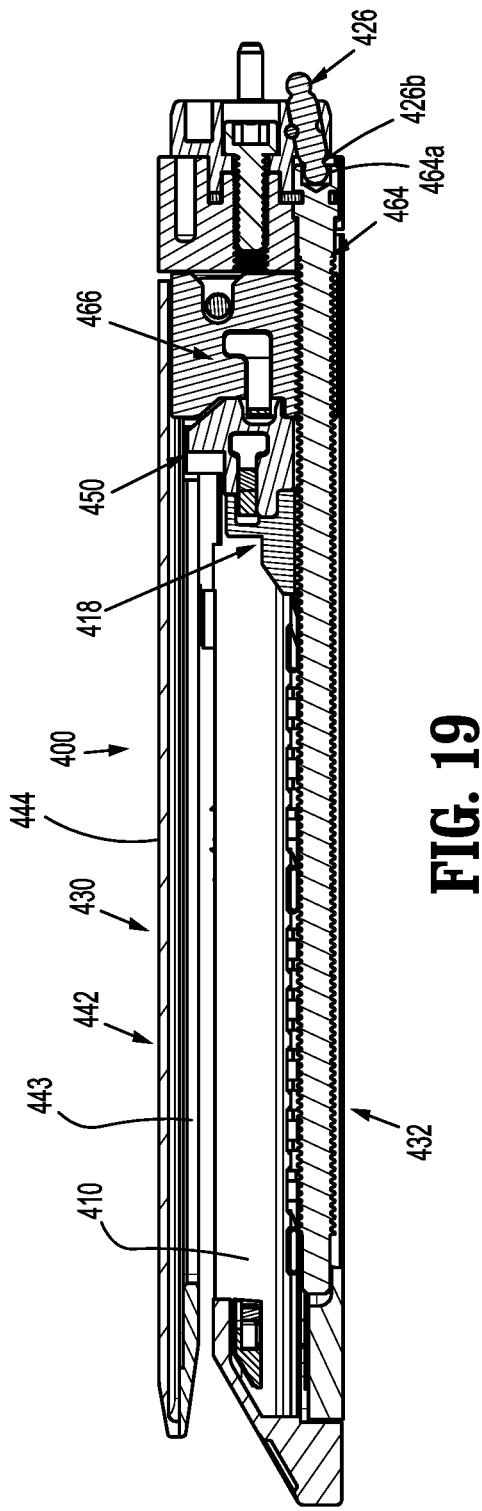

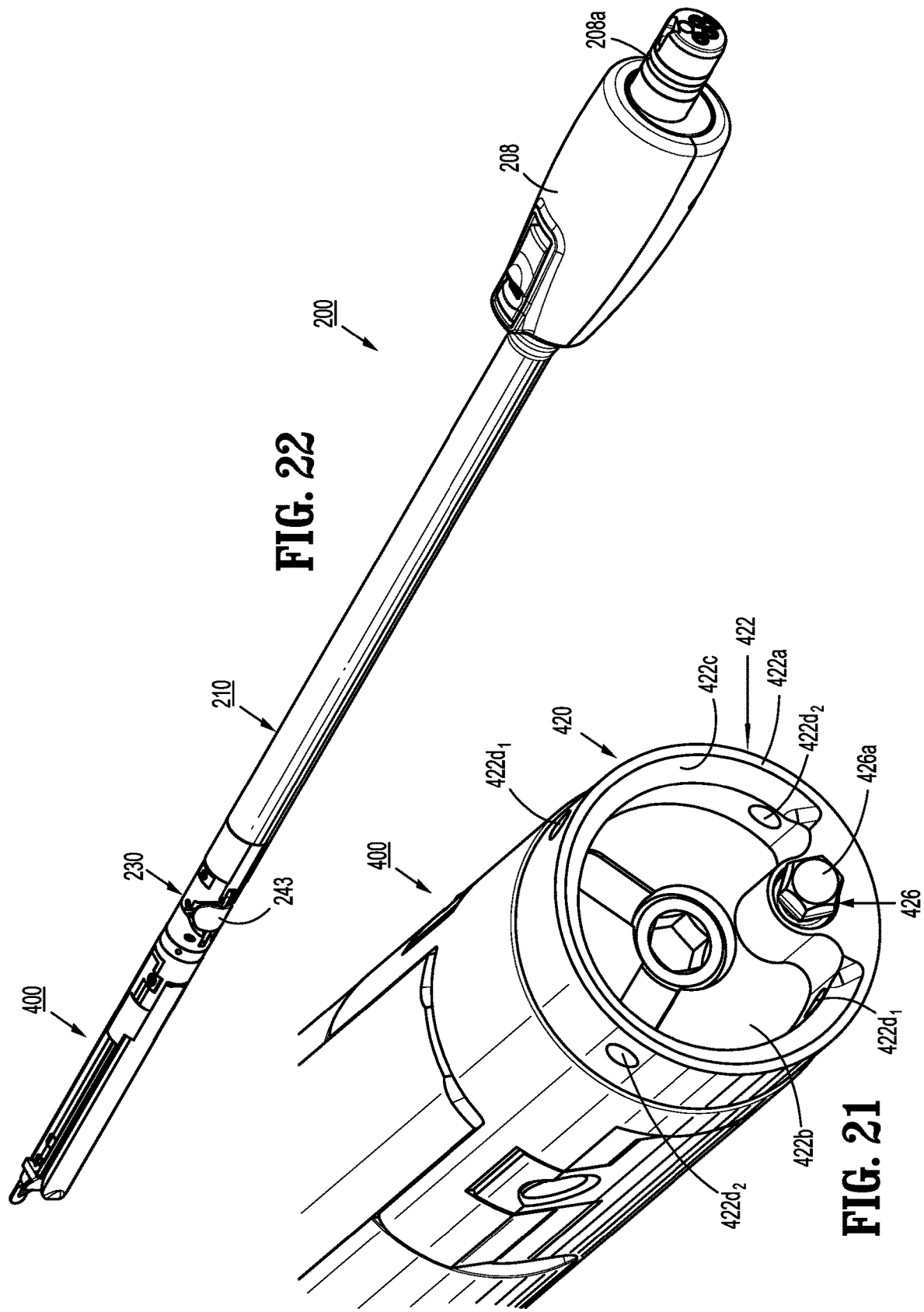

APPARATUS FOR ENDOSCOPIC PROCEDURES

CROSS-REFERENCE TO RELATED APPLICATIONS

The present application is a continuation of U.S. patent application Ser. No. 16/421,682, filed on May 24, 2019, now U.S. Pat. No. 11,154,282, which is a continuation of U.S. patent application Ser. No. 15/241,368, filed Aug. 19, 2016, now U.S. Pat. No. 10,299,772, which is a continuation of U.S. patent application Ser. No. 13/769,419, filed Feb. 18, 2013, now U.S. Pat. No. 9,421,003, the entire disclosures of which are incorporated by reference herein.

BACKGROUND

The present disclosure relates to surgical apparatus, devices and/or systems for performing endoscopic surgical procedures and methods of use thereof. More specifically, the present disclosure relates to electromechanical, hand-held surgical apparatus, devices and/or systems configured for use with removable disposable loading units and/or single use loading units for clamping, cutting and/or stapling tissue.

A number of surgical device manufacturers have developed product lines with proprietary drive systems for operating and/or manipulating electromechanical surgical devices. In many instances the electromechanical surgical devices include a handle assembly, which is reusable, and disposable loading units and/or single use loading units or the like that are selectively connected to the handle assembly prior to use and then disconnected from the handle assembly following use in order to be disposed of or in some instances sterilized for re-use.

Many of these electromechanical surgical devices are relatively expensive to manufacture, purchase and/or operate. There is a constant desire by manufactures and end users to develop electromechanical surgical devices that are relatively inexpensive to manufacture, purchase and/or operate yet still provide a large degree of operability.

Accordingly, a need exists for electromechanical surgical apparatus, devices and/or systems that are relatively economical from the development and manufacturing stages, to the selling/purchase stages, to the storing/shipping stages, to the use/operation stages, and on to the disposal and/or re-use stages while still providing an end user with a high degree of operability.

SUMMARY

The present disclosure relates to electromechanical, hand-held surgical apparatus, devices and/or systems configured for use with removable disposable loading units and/or single use loading units for clamping, cutting and/or stapling tissue.

According to an aspect of the present disclosure, an electromechanical surgical device is provided and includes an end effector configured to perform at least one function, the end effector including an input drive axle projecting therefrom; and a shaft assembly. The shaft assembly includes an outer tube; a rotatable drive shaft supported therein; a proximal neck housing supported at a distal end of the outer tube; a distal neck housing pivotally connected to the proximal neck housing, wherein a distal end of the distal neck housing is configured and adapted for operative connection with the end effector; a pivot pin interconnecting the proximal neck housing and the distal neck housing; and a gear train supported in the proximal neck housing, on the pivot pin, and in the distal neck housing.

The gear train includes a proximal gear rotatably supported in the proximal neck housing and being coupled to a distal end of the rotatable drive shaft; an intermediate gear rotatably supported on the pivot pin and being in operative engagement with the proximal gear; a distal gear rotatably supported in the distal neck housing and being in operative engagement with the intermediate gear; and a pair of output gears rotatably supported in the distal neck housing and each being in operative engagement with the distal gear, wherein each output gear defines a coupling socket each configured to selectively receive the drive axle of the end effector.

The end effector may include an upper jaw and a lower jaw movable with respect to one another between open and closed positions, wherein tissue contacting surfaces of the upper jaw and the lower jaw define a plane therebetween, and wherein the end effector is selectively connectable to the distal neck housing of the shaft assembly in one of a first orientation and a second orientation.

In the first orientation, the plane defined by the end effector may be oriented substantially orthogonal to a pivot axis defined by the pivot pin. In the second orientation, the plane defined by the end effector may be oriented substantially parallel to a pivot axis defined by the pivot pin.

In use, when the end effector is connected to the distal neck housing of the shaft assembly in the first orientation, the drive axle of the end effector may be coupled to the coupling socket of a first of the pair of output gears. Also in use, when the end effector is connected to the distal neck housing of the shaft assembly in the second orientation, the drive axle of the end effector may be coupled to the coupling socket of a second of the pair of output gears.

In an embodiment, a rotation of the drive shaft of the shaft assembly may result in rotation of both output gears.

The shaft assembly may have a straight configuration, and an angled configuration wherein the distal neck housing is pivoted about the pivot pin to a desired angled configuration. The gear train may transmit rotation from the drive shaft to both output gears when the shaft assembly is in either the straight configuration or the angled configuration.

An axis of rotation of the proximal gear may be co-axial with an axis of rotation of the drive shaft, wherein an axis of rotation of the distal gear may be co-axial with the axis of rotation of the drive shaft when the shaft assembly is in a straight configuration, and wherein an axis of rotation of each of the output gears may be parallel to the axis of rotation of the distal gear.

The axis of rotation of the distal gear may be oriented orthogonal to a pivot axis defined by the pivot pin.

The axis of rotation of each of the output gears may be disposed at approximately 90° to one another, relative to the axis of rotation of the distal gear.

The shaft assembly may include a release assembly configured for selective engagement with the end effector at a distal end of the shaft assembly, and may be actuatable from a proximal end of the shaft assembly.

The release assembly of the shaft assembly may include a pair of diametrically opposed connection pins supported in the distal neck housing. The release assembly may include an actuated condition in which the connection pins are retracted radially inward; and a non-actuated condition in which the connection pins project radially outward.

The end effector may include a coupling member defined by an annular wall, and wherein the coupling member may define a first pair of diametrically opposed attachment holes and a second pair of diametrically opposed attachment holes, wherein the first pair and the second pair of attachment holes may be offset approximately 90° relative to one another.

Each of the first pair and second pair of attachment holes may be configured to receive the pair of connection pins of the release assembly when the end effector is connected to the shaft assembly in one of the first orientation and the second orientation.

The release assembly of the shaft assembly may include a release button supported near a proximal end of the outer tube, and a release cable interconnecting the release button and the connection pins. In use, an actuation of the release button may exert a force on the release cable to actuate the connection pins from the non-actuated condition to the actuated condition.

The shaft assembly may further include an articulation rod at least partially slidably supported in the distal neck housing. The articulation rod may include a distal end; and a proximal end operatively connected to a rotatable drive shaft; wherein the articulation rod is offset a radial distance from a central longitudinal axis of the shaft assembly. The shaft assembly may further include an articulation link having a proximal end pivotally connected to the distal end of the articulation rod, and a distal end pivotally connected to the distal neck housing. In use, actuation of a rotatable drive shaft of the electromechanical surgical device that is connected to the articulation rod may cause the articulation rod to axially translate. Also in use, axial translation of the articulation rod may cause the distal neck housing to pivot off axis relative to the proximal neck housing.

According to another aspect of the present disclosure, an electromechanical surgical device is provided and comprises an end effector configured to perform at least one function, the end effector including an input drive axle projecting therefrom; and a shaft assembly. The shaft assembly includes an outer tube; a rotatable drive shaft supported therein; a proximal neck housing supported at a distal end of the outer tube; a distal neck housing pivotally connected to the proximal neck housing, wherein a distal end of the distal neck housing is configured and adapted for operative connection with the end effector; a pivot pin interconnecting the proximal neck housing and the distal neck housing; and a release assembly configured for selective engagement with the end effector at a distal end of the shaft assembly, and being actuatable from a proximal end of the shaft assembly, wherein the release assembly of the shaft assembly includes a pair of diametrically opposed connection pins supported in the distal neck housing. The release assembly includes an actuated condition in which the connection pins are retracted radially inward; and a non-actuated condition in which the connection pins project radially outward.

The end effector may include a coupling member defined by an annular wall, and wherein the coupling member may define a first pair of diametrically opposed attachment holes and a second pair of diametrically opposed attachment holes, wherein the first pair and the second pair of attachment holes are offset approximately 90° relative to one another.

Each of the first pair and second pair of attachment holes may be configured to receive the pair of connection pins of the release assembly when the end effector is connected to the shaft assembly in one of a first orientation and a second orientation oriented approximately 90° about a longitudinal axis thereof, relative to the first orientation.

The release assembly of the shaft assembly may include a release button supported near a proximal end of the outer tube, and a release cable interconnecting the release button and the connection pins. In use, an actuation of the release button may exert a force on the release cable to actuate the connection pins from the non-actuated condition to the actuated condition.

The shaft assembly may further include a gear train supported in the proximal neck housing, on the pivot pin, and in the distal neck housing. The gear train may include a proximal gear rotatably supported in the proximal neck housing and being coupled to a distal end of the rotatable drive shaft; an intermediate gear rotatably supported on the pivot pin and being in operative engagement with the proximal gear; a distal gear rotatably supported in the distal neck housing and being in operative engagement with the intermediate gear; and a pair of output gears rotatably supported in the distal neck housing and each being in operative engagement with the distal gear, wherein each output gear defines a coupling socket each configured to selectively receive the drive axle of the end effector.

The end effector may include an upper jaw and a lower jaw movable with respect to one another between open and closed positions, wherein tissue contacting surfaces of the upper jaw and the lower jaw defines a plane therebetween. The end effector may be selectively connectable to the distal neck housing of the shaft assembly in one of a first orientation and a second orientation.

In the first orientation, the plane defined by the end effector may be oriented substantially orthogonal to a pivot axis defined by the pivot pin. In the second orientation, the plane defined by the end effector may be oriented substantially parallel to a pivot axis defined by the pivot pin.

In use, when the end effector is connected to the distal neck housing of the shaft assembly in the first orientation, the drive axle of the end effector may be coupled to the coupling socket of a first of the pair of output gears. Also in use, when the end effector is connected to the distal neck housing of the shaft assembly in the second orientation, the drive axle of the end effector may be coupled to the coupling socket of a second of the pair of output gears.

A rotation of the drive shaft of the shaft assembly may result in rotation of both output gears.

The shaft assembly may have a straight configuration, and an angled configuration wherein the distal neck housing is pivoted about the pivot pin to a desired angled configuration between about 0° to about 90°.

The gear train may transmit rotation from the drive shaft to both output gears when the shaft assembly is in either the straight configuration or the angled configuration.

An axis of rotation of the proximal gear may be co-axial with an axis of rotation of the drive shaft, wherein an axis of rotation of the distal gear may be co-axial with the axis of rotation of the drive shaft when the shaft assembly is in a straight configuration, and wherein an axis of rotation of each of the output gears may be parallel to the axis of rotation of the distal gear.

The axis of rotation of the distal gear may be oriented orthogonal to a pivot axis defined by the pivot pin. The axis of rotation of each of the output gears may be disposed at approximately 90° to one another, relative to the axis of rotation of the distal gear.

The shaft assembly may further comprise an articulation rod at least partially slidably supported in the distal neck housing. The articulation rod may include a distal end; and a proximal end operatively connected to a rotatable drive shaft; wherein the articulation rod is offset a radial distance from a central longitudinal axis of the shaft assembly. The shaft assembly may include an articulation link having a proximal end pivotally connected to the distal end of the articulation rod, and a distal end pivotally connected to the distal neck housing. Actuation of a rotatable drive shaft of the electromechanical surgical device that is connected to the articulation rod may cause the articulation rod to axially translate. Axial translation of the articulation rod may cause the distal neck housing to pivot off axis relative to the proximal neck housing.

According to yet another embodiment of the present disclosure, an end effector for performing a surgical function and being connectable to an electromechanical power source is provided. The end effector comprises an upper jaw and a lower jaw, at least one of the upper jaw and the lower jaw being movable in relation to the other of the upper jaw and the lower jaw, wherein the lower jaw of the end effector is configured to selectively receive a cartridge assembly; a drive beam slidably supported in the lower jaw and being translatable through each of the upper jaw and the lower jaw to move the lower jaw relative to the upper; a cartridge assembly configured for loading into the lower jaw, the cartridge assembly including an actuation sled slidably supported therein and being configured to expel at least a portion of a plurality of staples loaded in the cartridge assembly upon a distal movement of the actuation sled from a proximal-most position; a drive screw rotatably supported in the lower jaw, wherein the drive beam is threadably supported on the drive screw, whereby rotation of the drive screw results in axial translation of the drive beam; and a proximal coupling member defined by a proximally extending annular wall defining a proximal facing opening, wherein a first pair of diametrically opposed attachment holes are formed in the annular wall, and a second pair of diametrically opposed attachment holes are formed in the annular wall, wherein the first pair and the second pair of attachment holes are offset approximately 90° relative to one another.

The annular wall of the coupling member may be angled radially inwardly and distally from a proximal-most edge thereof.

According to still another embodiment of the present disclosure, a shaft assembly for selectively interconnecting an end effector and an electromechanical power source is provided. The shaft assembly comprises an outer tube; a rotatable drive shaft supported therein; a proximal neck housing supported at a distal end of the outer tube; a distal neck housing pivotally connected to the proximal neck housing, wherein a distal end of the distal neck housing is configured and adapted for operative connection with the end effector; a pivot pin interconnecting the proximal neck housing and the distal neck housing; and a gear train supported in the proximal neck housing, on the pivot pin, and in the distal neck housing. The gear train includes a proximal gear rotatably supported in the proximal neck housing and being coupled to a distal end of the rotatable drive shaft; an intermediate gear rotatably supported on the pivot pin and being in operative engagement with the proximal gear; a distal gear rotatably supported in the distal neck housing and being in operative engagement with the intermediate gear; and a pair of output gears rotatably supported in the distal neck housing and each being in operative engagement with the distal gear, wherein each output gear defines a coupling socket each configured to selectively receive the drive axle of the end effector.

In use, a rotation of the drive shaft of the shaft assembly may result in rotation of both output gears.

The shaft assembly may have a straight configuration, and an angled configuration, between about 0° to about 90°, wherein the distal neck housing is pivoted about the pivot pin to a desired angled configuration.

The gear train may transmit rotation from the drive shaft to both output gears when the shaft assembly is in either the straight configuration or the angled configuration.

An axis of rotation of the proximal gear may be co-axial with an axis of rotation of the drive shaft, wherein an axis of rotation of the distal gear may be co-axial with the axis of rotation of the drive shaft when the shaft assembly is in a straight configuration, and wherein an axis of rotation of each of the output gears may be parallel to the axis of rotation of the distal gear.

The axis of rotation of the distal gear may be oriented orthogonal to a pivot axis defined by the pivot pin. The axis of rotation of each of the output gears may be disposed at approximately 90° to one another, relative to the axis of rotation of the distal gear.

The shaft assembly may further include a release assembly configured for selective engagement with the end effector at a distal end of the shaft assembly, and may be actuatable from a proximal end of the shaft assembly.

The release assembly may include a pair of diametrically opposed connection pins supported in the distal neck housing. The release assembly may include an actuated condition in which the connection pins are retracted radially inward; and a non-actuated condition in which the connection pins project radially outward.

The release assembly may include a release button supported near a proximal end of the outer tube, and a release cable interconnecting the release button and the connection pins.

In use, an actuation of the release button may exert a force on the release cable to actuate the connection pins from the non-actuated condition to the actuated condition.

The shaft assembly may further include an articulation rod at least partially slidably supported in the distal neck housing. The articulation rod may include a distal end; and a proximal end operatively connected to a rotatable drive shaft; wherein the articulation rod is off set a radial distance from a central longitudinal axis of the shaft assembly. The shaft assembly may include an articulation link having a proximal end pivotally connected to the distal end of the articulation rod, and a distal end pivotally connected to the distal neck housing. In use, actuation of a rotatable drive shaft of the electromechanical surgical device that is connected to the articulation rod may cause the articulation rod to axially translate. Also in use, axial translation of the articulation rod may cause the distal neck housing to pivot off axis relative to the proximal neck housing.

Further details and aspects of exemplary embodiments of the present invention are described in more detail below with reference to the appended figures.

BRIEF DESCRIPTION OF THE DRAWINGS

Embodiments of the present disclosure are described herein with reference to the accompanying drawings, wherein:

FIG. 5 is a rear, perspective view of the shaft assembly of FIGS. 1, 3 and 4, with outer covers or housing removed therefrom;

FIG. 6 is a rear, perspective view of the shaft assembly illustrated in FIG. 5, with an outer cover or housing of a proximal coupling member removed therefrom;

FIG. 7 is an enlarged, left-side, perspective view of a proximal end portion of the shaft assembly illustrated in FIG. 6;

FIG. 12 is a rear, perspective view of the articulating neck assembly of FIG. 11 with housing portions removed therefrom;

FIG. 13 is a front, perspective view of the articulating neck assembly of FIG. 11 with housing portions removed therefrom;

FIG. 14 is a rear, perspective view, partially broken away, of the shaft assembly of FIGS. 1, 3 and 4, with outer covers or housing removed therefrom;

FIG. 15 is a cross-sectional view as taken and viewed along 15-15 of FIG. 14;

FIG. 15A is an enlarged, perspective view, with parts separated, of a release button of the release assembly;

FIG. 16 is an enlarged, rear perspective view of a distal end portion of the shaft assembly of FIG. 4;

FIG. 18 is a side, elevational view of an end effector according to an embodiment of the present disclosure;

FIG. 19 is a longitudinal, cross-sectional view of the end effector of FIG. 18;

FIG. 21 is an enlarged, rear, perspective view of a proximal end of the end effector of FIGS. 18-20;

FIG. 22 is a perspective view illustrating the end effector and shaft assembly connected to one another;

DETAILED DESCRIPTION

Figure 1:
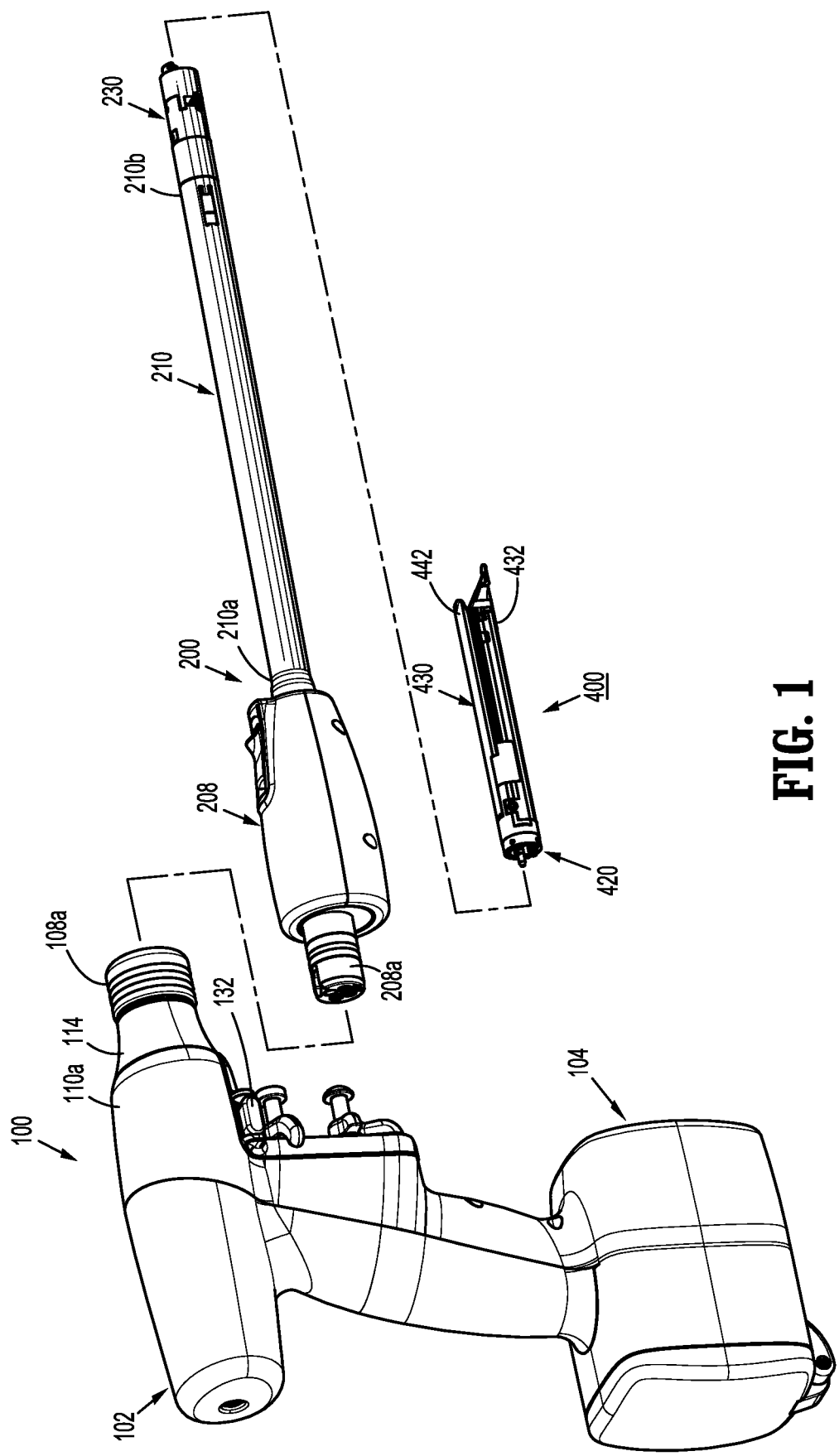
FIG. 1 is a perspective view, with parts separated, of an electromechanical surgical system according to an embodiment of the present disclosure.

Embodiments of the presently disclosed electromechanical surgical system, apparatus and/or device are described in detail with reference to the drawings, in which like reference numerals designate identical or corresponding elements in each of the several views. As used herein the term "distal" refers to that portion of the electromechanical surgical system, apparatus and/or device, or component thereof, that are farther from the user, while the term "proximal" refers to that portion of the electromechanical surgical system, apparatus and/or device, or component thereof, that are closer to the user.

Figure 2:
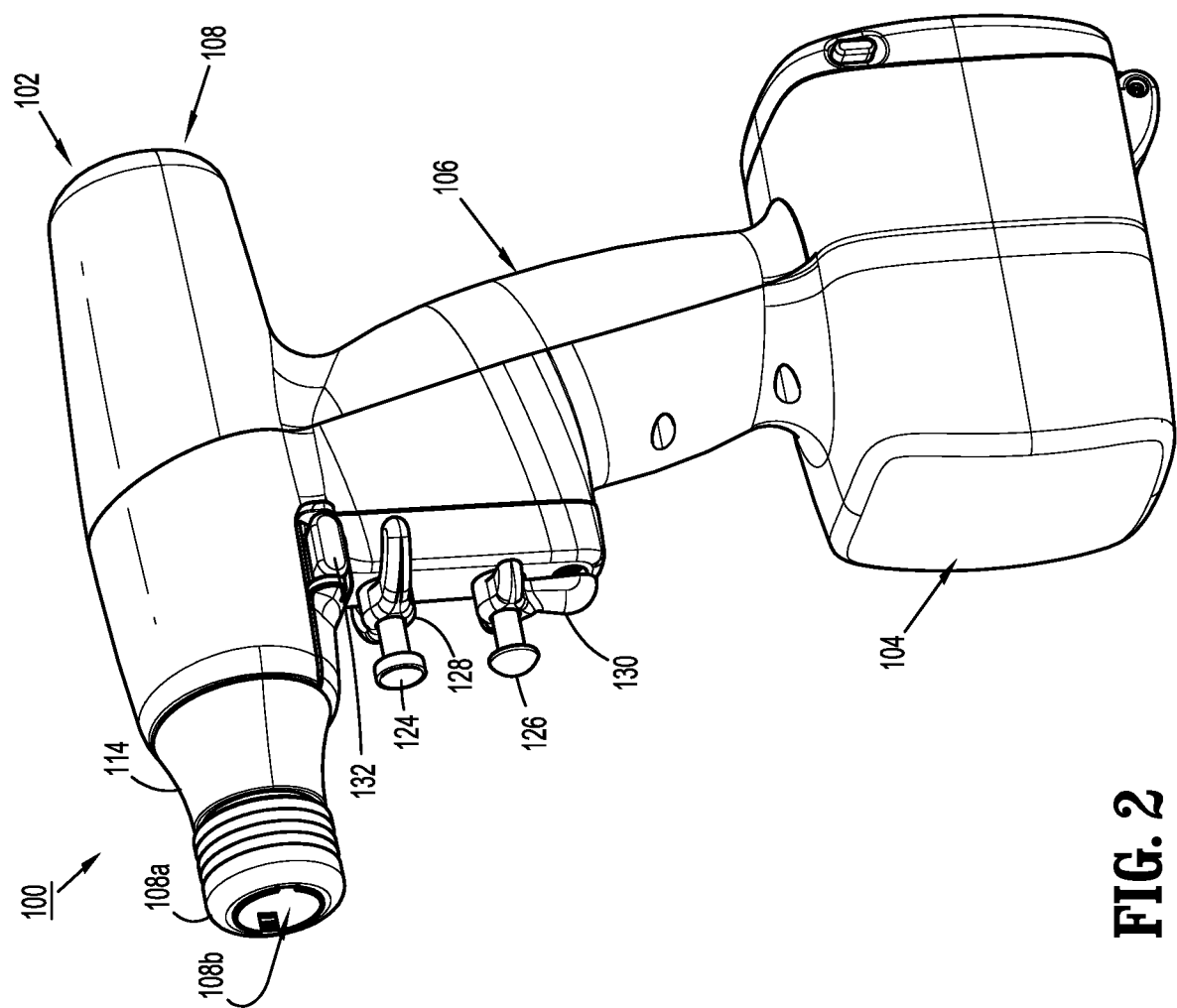
FIG. 2 is a perspective view of a powered surgical device of the electromechanical surgical system of FIG. 1.
Figure 3:
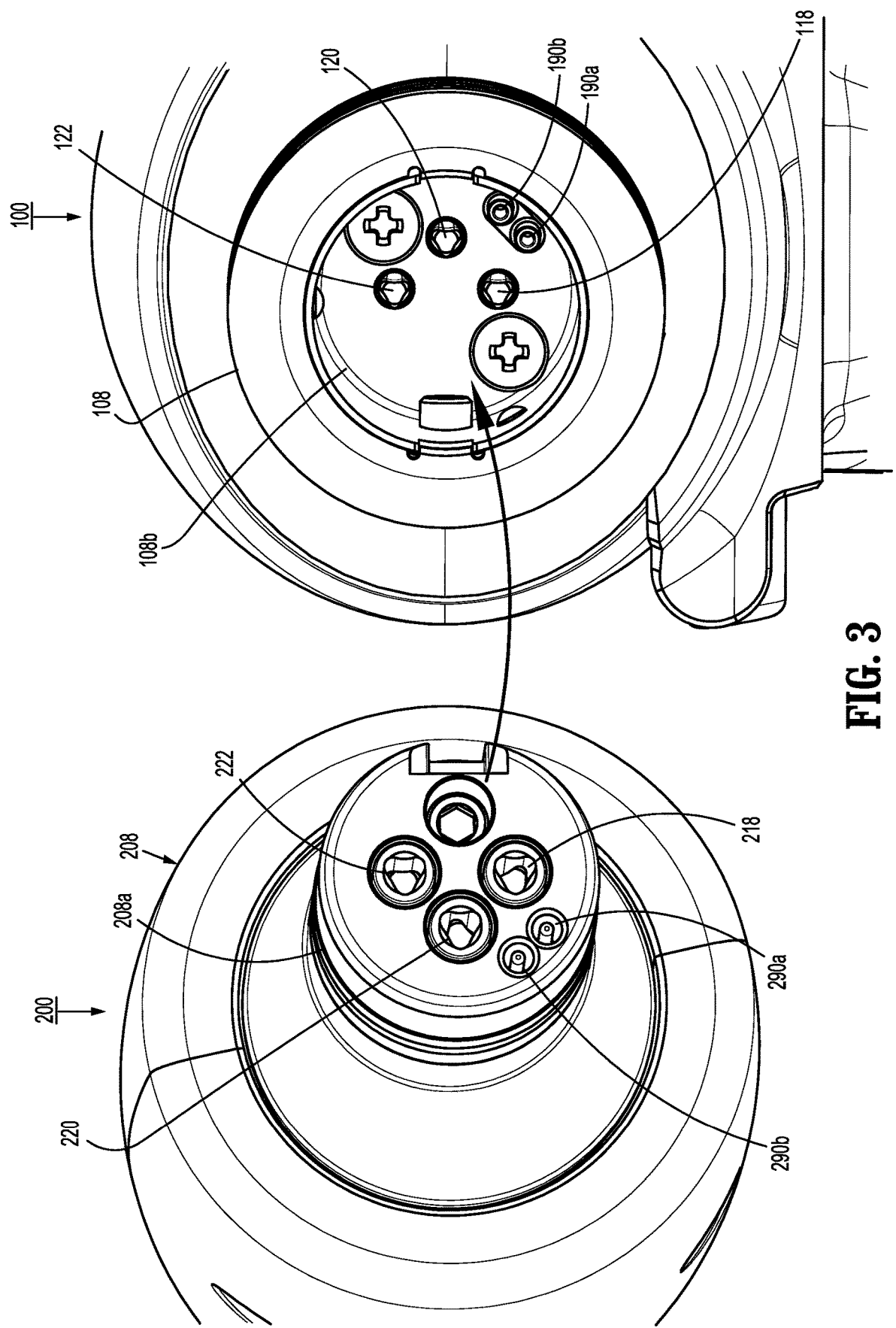
FIG. 3 is a rear, perspective view of a shaft assembly and a powered surgical device, of the electromechanical surgical system of FIG. 1, illustrating a connection therebetween.

Referring initially to FIGS. 1-3, an electromechanical, hand-held, powered surgical system, in accordance with an embodiment of the present disclosure is shown and generally designated 10. Electromechanical surgical system 10 includes a surgical apparatus or device in the form of an electromechanical, hand-held, powered surgical device 100 that is configured for selective attachment thereto of a plurality of different end effectors 400, via an adapter or shaft assembly 200, that are each configured for actuation and manipulation by the electromechanical, hand-held, powered surgical device 100. In particular, surgical device 100 is configured for selective connection with shaft assembly 200, and, in turn, shaft assembly 200 is configured for selective connection with any one of a plurality of different end effectors 400.

Reference may be made to International Application No. PCT/US2008/077249, filed Sep. 22, 2008 (Inter. Pub. No. WO 2009/039506) and U.S. patent application Ser. No. 12/622,827, filed on Nov. 20, 2009, now U.S. Pat. No. 10,588,629, the entire content of each of which being incorporated herein by reference, for a detailed description of the construction and operation of exemplary electromechanical, hand-held, powered surgical device 100.

Generally, as illustrated in FIGS. 1-3, surgical device 100 includes a handle housing 102 having a lower housing portion 104, an intermediate housing portion 106 extending from and/or supported on lower housing portion 104, and an upper housing portion 108 extending from and/or supported on intermediate housing portion 106. Handle housing 102 defines a cavity therein in which a circuit board (not shown) and a drive mechanism (not shown) are situated.

The circuit board is configured to control the various operations of surgical device 100, as will be set forth in additional detail below. In accordance with the present disclosure, handle housing 102 provides a housing in which a rechargeable battery (not shown), is removably situated. The battery is configured to supply power to any of the electrical components of surgical device 100.

Upper housing portion 108 of handle housing 102 defines a nose or connecting portion 108a configured to accept a corresponding shaft coupling assembly 208a of transmission housing 208 of shaft assembly 200. As seen in FIGS. 2 and 3, connecting portion 108a of upper housing portion 108 of surgical device 100 has a cylindrical recess 108b that receives shaft coupling assembly 208a of transmission housing 208 of shaft assembly 200 when shaft assembly 200 is mated to surgical device 100. Connecting portion 108a houses three rotatable drive connectors 118, 120, 122, each independently actuatable and rotatable by the drive mechanism (not shown) housed within handle housing 102.

Figure 4:
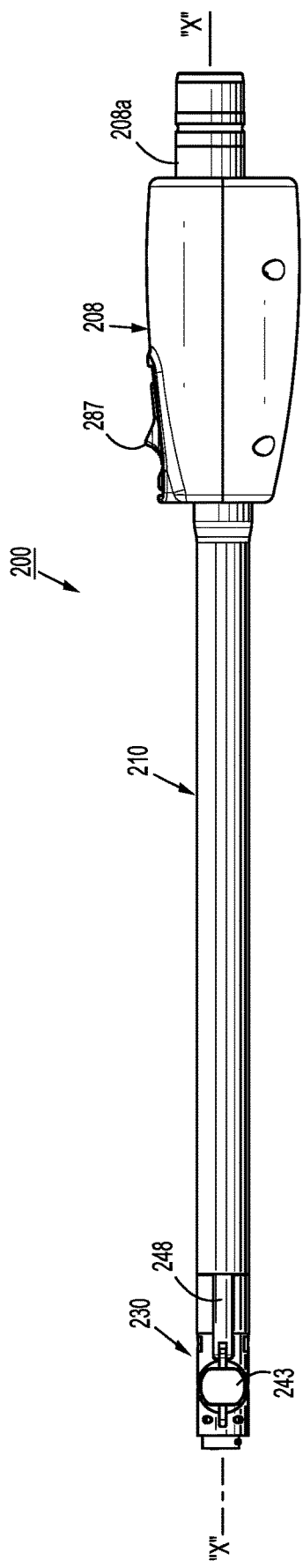
FIG. 4 is a side, elevational view of the shaft assembly of FIGS. 1 and 3.

Upper housing portion 108 of handle housing 102 provides a housing in which the drive mechanism (not shown) is situated. The drive mechanism is configured to drive shafts and/or gear components in order to perform the various operations of surgical device 100. In particular, the drive mechanism is configured to drive shafts and/or gear components in order to selectively move end effector 400 relative to shaft assembly 200; to rotate shaft assembly 200 and/or end effector 400, about a longitudinal axis "X" (see FIG. 4), relative to handle housing 102; to move an upper jaw or anvil assembly 442 of end effector 400 relative to a lower jaw or cartridge assembly 410 of end effector 400, and/or to fire a stapling and cutting cartridge within cartridge assembly 410 of end effector 400.

Figure 8:
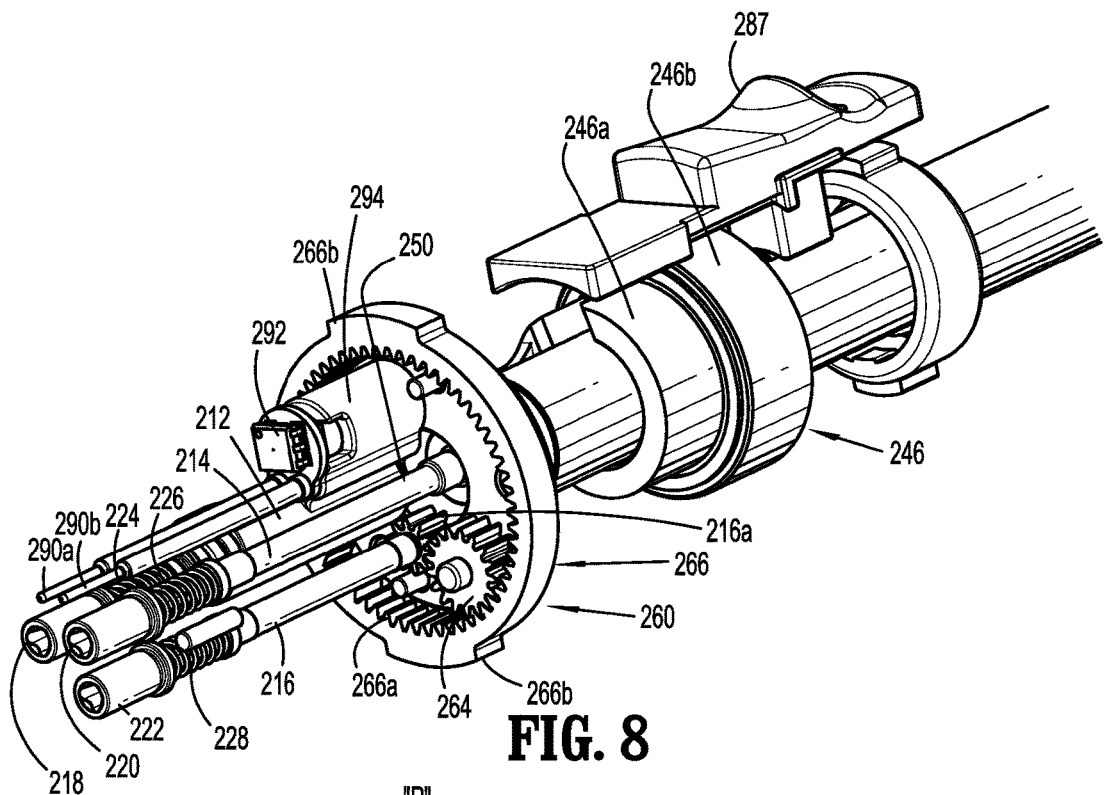
FIG. 8 is an enlarged, right-side, perspective view of a proximal end portion of the shaft assembly illustrated in FIG. 6.
Figure 9:
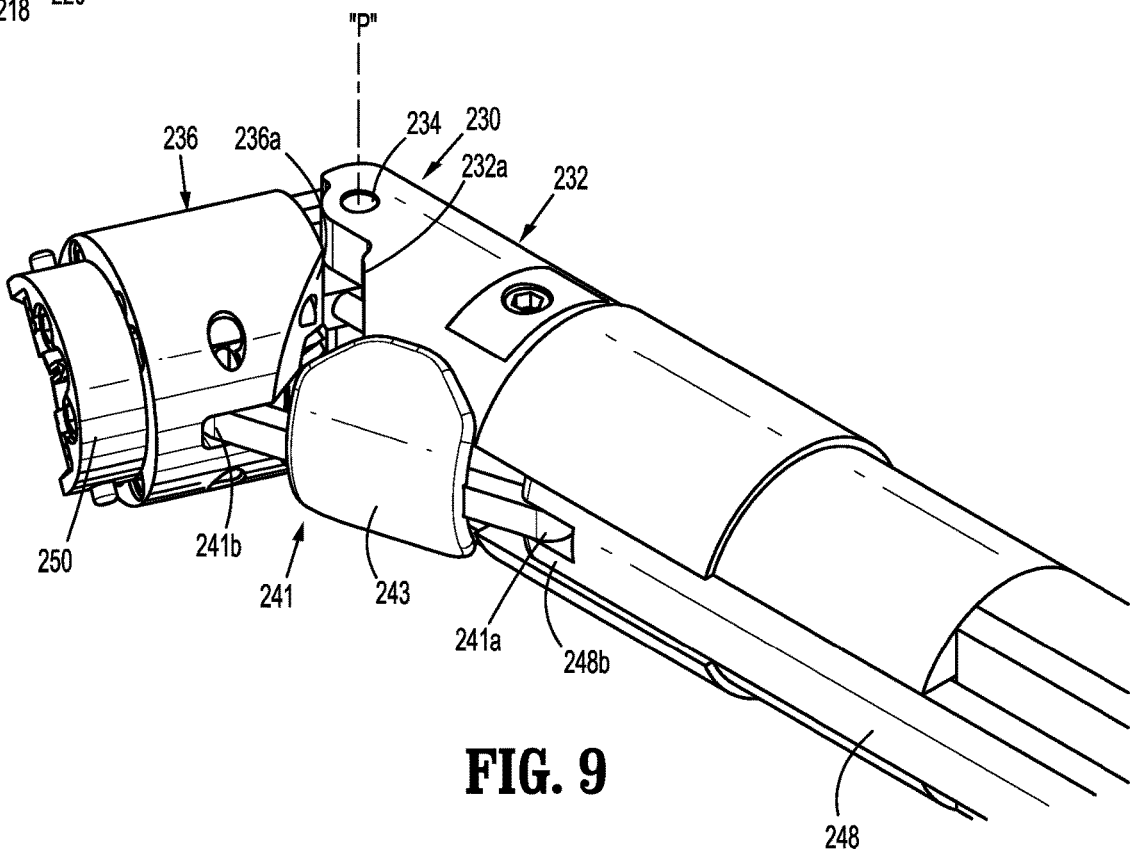
FIG. 9 is an enlarged, perspective view of a distal end portion of the shaft assembly illustrated in FIG. 6.
Figure 11:
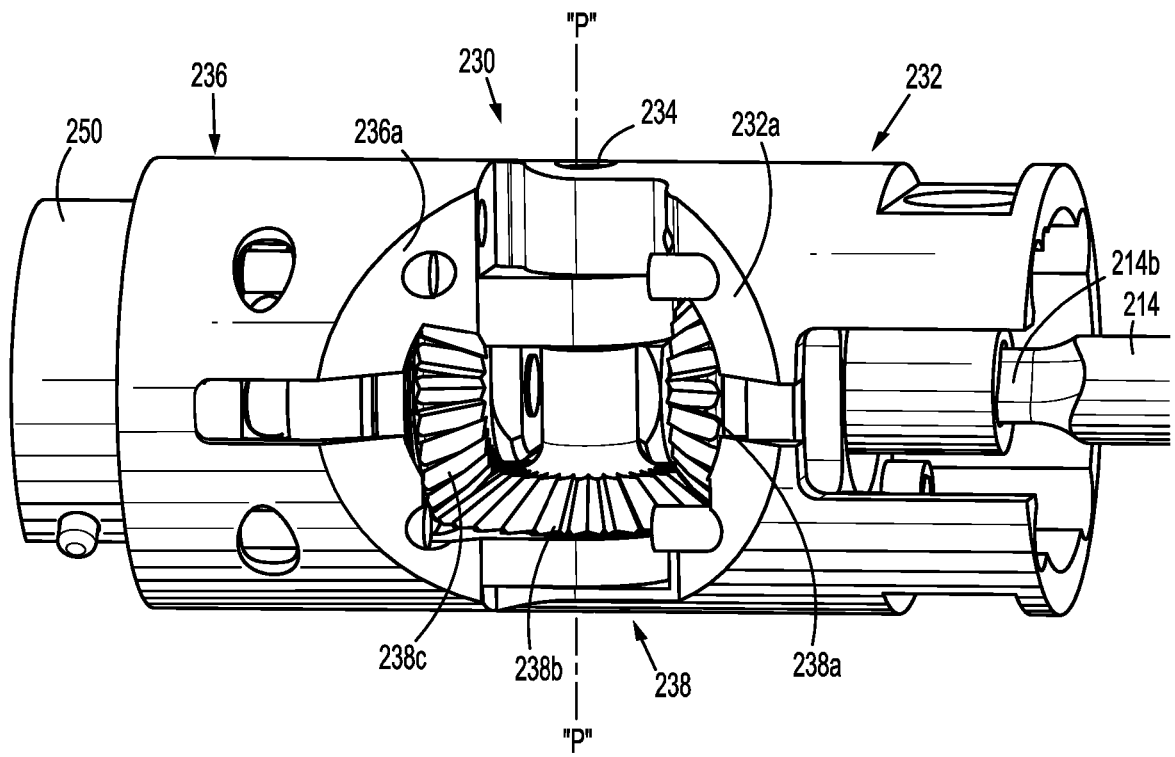
FIG. 11 is a side, elevational view of an articulating neck assembly of the shaft assembly of FIGS. 1 and 3-9.

In use, when shaft assembly 200 is mated to surgical device 100, each of rotatable drive connectors 118, 120, 122 of surgical device 100 couples with a corresponding rotatable connector sleeve 218, 220, 222 of shaft assembly 200 (see FIGS. 3, 7 and 8). In this regard, the interface between corresponding first drive connector 118 and first connector sleeve 218, the interface between corresponding second drive connector 120 and second connector sleeve 220, and the interface between corresponding third drive connector 122 and third connector sleeve 222 are keyed such that rotation of each of drive connectors 118, 120, 122 of surgical device 100 causes a corresponding rotation of the corresponding connector sleeve 218, 220, 222 of shaft assembly 200.

The mating of drive connectors 118, 120, 122 of surgical device 100 with connector sleeves 218, 220, 222 of shaft assembly 200 allows rotational forces to be independently transmitted via each of the three respective connector interfaces. The drive connectors 118, 120, 122 of surgical device 100 are configured to be independently rotated by the drive mechanism. In this regard, a function selection module (not shown) of the drive mechanism selects which drive connector or connectors 118, 120, 122 of surgical device 100 is to be driven by an input drive component (not shown) of the drive mechanism.

Since each of drive connectors 118, 120, 122 of surgical device 100 has a keyed and/or substantially non-rotatable interface with respective connector sleeves 218, 220, 222 of shaft assembly 200, when shaft assembly 200 is coupled to surgical device 100, rotational force(s) are selectively transferred from the drive mechanism of surgical device 100 to shaft assembly 200, and on to end effector 400, as will be discussed in greater detail below.

The selective rotation of drive connector(s) 118, 120 and/or 122 of surgical device 100 allows surgical device 100 to selectively actuate different functions of end effector 400. As will be discussed in greater detail below, selective and independent rotation of first drive connector 118 of surgical device 100 corresponds to the selective and independent rotation of end effector 400 about longitudinal axis "X" (see FIG. 4) relative to handle housing 102 of surgical device 100. Also, the selective and independent rotation of second drive connector 120 of surgical device 100 corresponds to the selective and independent opening and closing of end effector 400, and driving of a stapling/cutting component of end effector 400. Additionally, the selective and independent rotation of third drive connector 122 of surgical device 100 corresponds to the selective and independent articulation of end effector 400 transverse to longitudinal axis "X" (see FIG. 4).

In accordance with the present disclosure, the drive mechanism may include a selector gearbox assembly (not shown); a function selection module (not shown), located proximal to the selector gearbox assembly, that functions to selectively move gear elements within the selector gearbox assembly into engagement with a second motor (not shown). The drive mechanism may be configured to selectively drive one of drive connectors 118, 120, 122 of surgical device 100, at a given time. Alternatively, the drive mechanism may be configured and capable of simultaneously driving all drive connectors 118, 120, 122, or any selected two of the drive connectors 118, 120, 122.

As illustrated in FIGS. 1 and 2, handle housing 102 supports a pair of finger-actuated control buttons 124, 126 and/or rocker device(s) 130 (only one rocker device being shown). Each one of the control buttons 124, 126 and rocker device(s) 130 includes a respective magnet (not shown) that is moved by the actuation of an operator.

As illustrated in FIGS. 1-3, surgical device 100 is configured for selective connection with shaft assembly 200, and, in turn, shaft assembly 200 is configured for selective connection with end effector 400. Turning now to FIGS. 1 and 3-17C, shaft assembly 200 will be shown in detail and described. Shaft assembly 200 is configured to communicate the rotational forces of first, second and third rotatable drive connectors 118, 120, and 122 of surgical device 100 to end effector 400. As mentioned above, shaft assembly 200 is configured for selective connection to surgical device 100.

As seen in FIGS. 1 and 3-9, shaft assembly 200 includes an elongate, substantially rigid, tubular body 210 having a proximal end 210a and a distal end 210b; a transmission housing 208 connected to proximal end 210a of tubular body 210 and being configured for selective connection to surgical device 100; and an articulating neck assembly 230 connected to distal end 210b of elongate body portion 210.

Transmission housing 208 and tubular body 210 are configured and dimensioned to house the components of shaft assembly 200. Tubular body 210 is dimensioned for endoscopic insertion, in particular, that outer tube is passable through a typical trocar port, cannula or the like. Transmission housing 208 is dimensioned to not enter the trocar port, cannula or the like.

Transmission housing 208 of shaft assembly 200 is configured and adapted to connect to connecting portion 108a of upper housing portion 108 of surgical device 100. As seen in FIGS. 1, 3-5, 14 and 22, transmission housing 208 of shaft assembly 200 includes a shaft coupling assembly 208a supported at a proximal end thereof. Shaft coupling assembly 208a is configured and adapted to connect to connecting portion 108a of upper housing portion 108 of distal half-section 110a of surgical device 100.

Transmission housing 208, and particularly shaft coupling assembly 208a, rotatably supports a first rotatable proximal drive shaft 212, a second rotatable proximal drive shaft 214, and a third rotatable proximal drive shaft 216 therein.

Shaft coupling assembly 208a is also configured to rotatably support first, second and third connector sleeves 218, 220 and 222, respectively. Each of connector sleeves 218, 220, 222 is configured to mate with respective first, second and third drive connectors 118, 120, 122 of surgical device 100, as described above. Each of connector sleeves 218, 220, 222 is further configured to mate with a proximal end of respective first, second and third proximal drive shafts 212, 214, 216.

Shaft coupling assembly 208a of transmission housing 208 also includes a first, a second and a third biasing member 224, 226 and 228 disposed distally of respective first, second and third connector sleeves 218, 220, 222. Each of biasing members 224, 226 and 228 is disposed about respective first, second and third rotatable proximal drive shaft 212, 214 and 216. Biasing members 224, 226 and 228 act on respective connector sleeves 218, 220 and 222 to help maintain connector sleeves 218, 220 and 222 engaged with the distal end of respective rotatable drive connectors 118, 120, 122 of surgical device 100 when shaft assembly 200 is connected to surgical device 100.

In particular, first, second and third biasing members 224, 226 and 228 function to bias respective connector sleeves 218, 220 and 222 in a proximal direction. In this manner, during assembly of shaft assembly 200 to surgical device 100, if first, second and/or third connector sleeves 218, 220 and/or 222 is/are misaligned with the drive connectors 118, 120, 122 of surgical device 100, first, second and/or third biasing member(s) 224, 226 and/or 228 are compressed. Thus, when surgical device 100 is operated, drive connectors 118, 120, 122 of surgical device 100 will rotate and first, second and/or third biasing member(s) 224, 226 and/or 228 will cause respective first, second and/or third connector sleeve(s) 218, 220 and/or 222 to slide back proximally, effectively coupling drive connectors 118, 120, 122 of surgical device 100 to first, second and/or third proximal drive shaft(s) 212, 214 and 216 of shaft coupling assembly 208a of transmission housing 208.

Shaft assembly 200 includes a plurality of force/rotation transmitting/converting assemblies, each disposed within transmission housing 208 and tubular body 210. Each force/rotation transmitting/converting assembly is configured and adapted to transmit/convert a speed/force of rotation (e.g., increase or decrease) of first, second and third rotatable drive connectors 118, 120 and 122 of surgical device 100 before transmission of such rotational speed/force to end effector 400.

Specifically, shaft assembly 200 includes a first, a second and a third force/rotation transmitting/converting assembly 240, 250, 260, respectively, disposed within transmission housing 208 and tubular body 210. Each force/rotation transmitting/converting assembly 240, 250, 260 is configured and adapted to transmit or convert a rotation of a first, second and third drive connector 118, 120, 122 of surgical device 100 into axial translation of articulation bar 248 of shaft assembly 200, to effectuate articulating of end effector 400; a rotation of a ring gear 266 of shaft assembly 200, to effectuate rotation of shaft assembly 200; or a second proximal drive shaft 214 of shaft assembly 200 to effectuate closing, opening and firing of end effector 400.

As seen in FIGS. 5-8, first force/rotation transmitting/converting assembly 240 includes first rotatable proximal drive shaft 212, which, as described above, is rotatably supported within transmission housing 208. First rotatable proximal drive shaft 212 includes a non-circular or shaped proximal end portion configured for connection with first connector sleeve 218 which is connected to respective first connector 118 of surgical device 100. First rotatable proximal drive shaft 212 includes a distal end portion 212b having a threaded outer profile or surface.

First force/rotation transmitting/converting assembly 240 further includes a drive coupling nut 244 rotatably coupled to threaded distal end portion 212b of first rotatable proximal drive shaft 212, and which is slidably disposed within transmission housing 208. Drive coupling nut 244 is slidably keyed within transmission housing 208 so as to be prevented from rotation as first rotatable proximal drive shaft 212 is rotated. In this manner, as first rotatable proximal drive shaft 212 is rotated, drive coupling nut 244 is translated along threaded distal end portion 212b of first rotatable proximal drive shaft 212 and, in turn, through and/or along transmission housing 208.

First force/rotation transmitting/converting assembly 240 further includes a thrust bearing assembly 246 having a first bearing 246a secured to drive coupling nut 244, and a second bearing 246b rotatably connected to first bearing 246a. First force/rotation transmitting/converting assembly 240 also includes an articulation bar 248 having a proximal end 248a secured or connected to second bearing 246b. A distal end 248b of articulation bar 248 extends through tubular body 210.

In operation, as first rotatable proximal drive shaft 212 is rotated, due to a rotation of first connector sleeve 218, as a result of the rotation of the first respective drive connector 118 of surgical device 100, threaded distal end portion 212b of first rotatable proximal drive shaft 212 is rotated. Thus, as first rotatable proximal drive shaft 212 is rotated, drive coupling nut 244 is caused to be translated axially along threaded distal portion 212b of first rotatable proximal drive shaft 212.

As drive coupling nut 244 is caused to be translated axially along first rotatable proximal drive shaft 212, thrust bearing 246 and, in turn, articulation bar 248, are caused to be translated axially relative to tubular body 210. As will be described in greater detail below, as articulation bar 248 is axially translated, articulation bar 248 causes articulating neck assembly 230 of shaft assembly 200 to articulate and, in turn, causes end effector 400 to articulate when end effector 400 is connected to shaft assembly 200.

With reference to FIGS. 5-8, second force/rotation transmitting/converting assembly 250 of shaft assembly 200 includes second rotatable proximal drive shaft 214 rotatably supported within transmission housing 208 and tubular body 210. Second rotatable proximal drive shaft 214 includes a non-circular or shaped proximal end portion configured for connection with second connector sleeve 220 which is connected to respective second connector 120 of surgical device 100. Second rotatable proximal drive shaft 214 further includes a distal end portion 214b (see FIGS. 11-13) having a non-circular or shaped transverse cross-sectional profile. Distal end portion 214b of second rotatable proximal drive shaft 214 extends to proximal neck housing 232 of articulating neck assembly 230. In accordance with the present disclosure, second rotatable proximal drive shaft 214 defines an axis of rotation that is substantially co-incident or co-axial with a central longitudinal axis of tubular body 210.

In operation, as illustrated in FIGS. 5-8, as second rotatable proximal drive shaft 214 is rotated due to a rotation of second connector sleeve 220, as a result of the rotation of the second drive connector 120 of surgical device 100, said rotation is transmitted directly to first or proximal bevel gear 238a of articulating neck assembly 230 of shaft assembly 200, to effectuate a closure and a firing of end effector 400, as will be discussed in greater detail below.

As also seen in FIGS. 5-8 and as mentioned above, shaft assembly 200 includes a third force/rotation transmitting/converting assembly 260 supported in transmission housing 208. Third force/rotation transmitting/converting assembly 260 includes a rotation ring gear 266 fixedly supported in transmission housing 208. Ring gear 266 defines an internal array of gear teeth 266a. Ring gear 266 includes a pair of diametrically opposed, radially extending protrusions 266b projecting from an outer edge thereof. Protrusions 266b are disposed within recesses (not shown) defined in an inner surface of transmission housing 208, such that rotation of ring gear 266 results in rotation of transmission housing 208.

Third force/rotation transmitting/converting assembly 260 further includes third rotatable proximal drive shaft 216 which, as described above, is rotatably supported within transmission housing 208. Third rotatable proximal drive shaft 216 includes a non-circular or shaped proximal end portion configured for connection with third connector sleeve 222 which is connected to respective third connector 122 of surgical device 100. Third rotatable proximal drive shaft 216 includes a spur gear 216a keyed to a distal end thereof. A reversing spur gear 264 inter-engages spur gear 216a of third rotatable proximal drive shaft 216 to gear teeth 266a of ring gear 266.

In operation, as illustrated in FIGS. 5-8, as third rotatable proximal drive shaft 216 is rotated, due to a rotation of third connector sleeve 222, as a result of the rotation of the third drive connector 122 of surgical device 100, spur gear 216a of third rotatable proximal drive shaft 216 engages reversing gear 264 causing reversing gear 264 to rotate. As reversing gear 264 rotates, ring gear 266 also rotates thereby causing transmission housing 208 to rotate. As transmission housing 208 is rotated, tubular body 210 is caused to be rotated about longitudinal axis "X" of shaft assembly 200. As tubular body 210 is rotated, end effector 400, that is connected to distal neck housing 236 of articulating neck assembly 230 of shaft assembly 200, is also caused to be rotated about a longitudinal axis of shaft assembly 200.

Turning now to FIGS. 5, 6, 9 and 10A-13, articulating neck assembly 230 is shown and described. Articulating neck assembly 230 includes a proximal neck housing 232; and a distal neck housing 236 pivotally connected to and extending distally from proximal neck housing 232 by a pivot pin 234. Pivot pin 234 defines a pivot axis "P" (see FIGS. 9 and 11-13) that is oriented orthogonal to the longitudinal axis "X" and extends through the longitudinal axis "X".

Articulating neck assembly 230 includes a gear train 238 having a first or proximal bevel gear 238a rotatably supported in proximal neck housing 232, a second or intermediate bevel gear 238b supported on pivot pin 234 and enmeshed with first bevel gear 238a, and a third or distal bevel gear 238c rotatably supported in distal neck housing 236 and enmeshed with second or intermediate bevel gear 238b. It is contemplated that each of first or proximal bevel gear 238a and third or distal bevel gear 238c share a common axis of rotation which is co-incident or co-axial with the central longitudinal axis "X" of shaft assembly 200, when articulating neck assembly 230 is in a non-articulated condition.

First or proximal bevel gear 238a is non-rotatably coupled to distal end portion 214b of second rotatable proximal drive shaft 214. In this manner, as second rotatable proximal drive shaft 214 is rotated, as described above, said rotation is transmitted to first or proximal bevel gear 238a.

Third or distal bevel gear 238c includes a spur gear 238d non-rotatably connected thereto via a rotation shaft or pin 238e. In this manner, as first or proximal bevel gear 238a is rotated, as described above, said rotation is transmitted to second or intermediate bevel gear 238b and, in turn, on to third or distal bevel gear 238c. As third or distal bevel gear 238c is rotated, said rotation is transmitted to spur gear 238d due to the non-rotatably inter-connection by shaft or pin 238e.

While gear train 238 has been shown and described using bevel gears, it is contemplated that gear train 238 may include at least one face gear or the like to achieve the intended purpose of transferring rotation across a pivot point.

As seen in FIGS. 5, 6, 9 and 10A-13, distal neck portion 236 of articulating neck assembly 230 rotatably supports a pair of output gears 239a, 239b, each enmeshed with spur gear 238d. Each output gear 239a, 239b defines a respective coupling socket $239a_1, 239b_1$. In this manner, as spur gear 238d is rotated, as described above, said rotation is transmitted to both output gears 239a, 239b. Each coupling socket $239a_1, 239b_1$ is configured and dimensioned to selectively receive a proximal head 426a of a drive axle 426 of end effector 400, as will be discussed in greater detail below. Moreover, output gears 239a, 239b are arranged to have axes of rotation which are parallel to the longitudinal axis "X" and which are disposed substantially at 90° relative to one another, or any other appropriate or desired angular separation from one another.

Articulating neck assembly 230 includes an articulation link 241 having a proximal end 241a pivotally connected to distal end 248b of articulation bar 248. A distal end 241b of articulation link 241 is pivotally connected to distal neck housing 236, at a location offset a transverse distance from the longitudinal axis "X".

Figure 17:
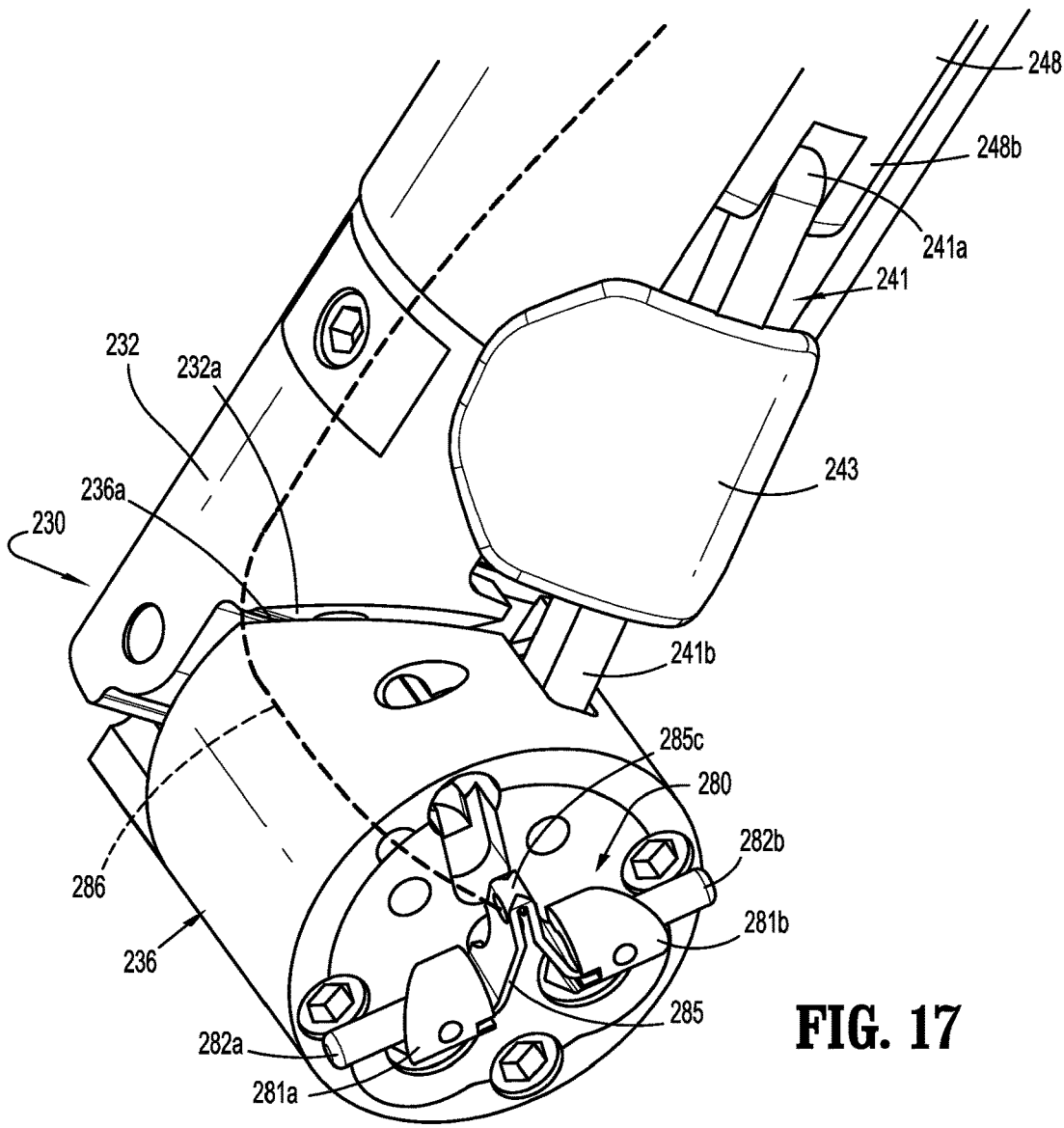
FIG. 17 is an enlarged, rear perspective view of a distal-most end portion of the shaft assembly of FIG. 4.
Figure 23:
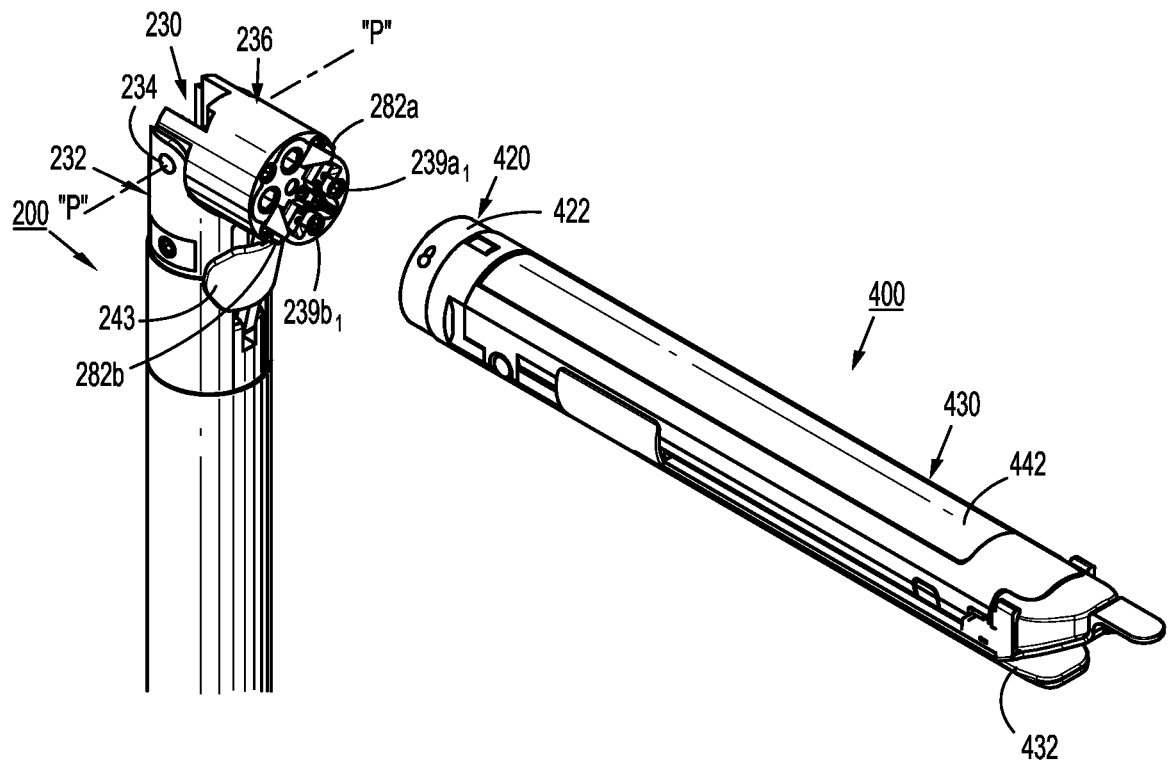
FIG. 23 is a perspective view, illustrating the distal end of the shaft assembly in an articulated condition and the end effector being connected thereto while in a first angular orientation.
Figure 24:
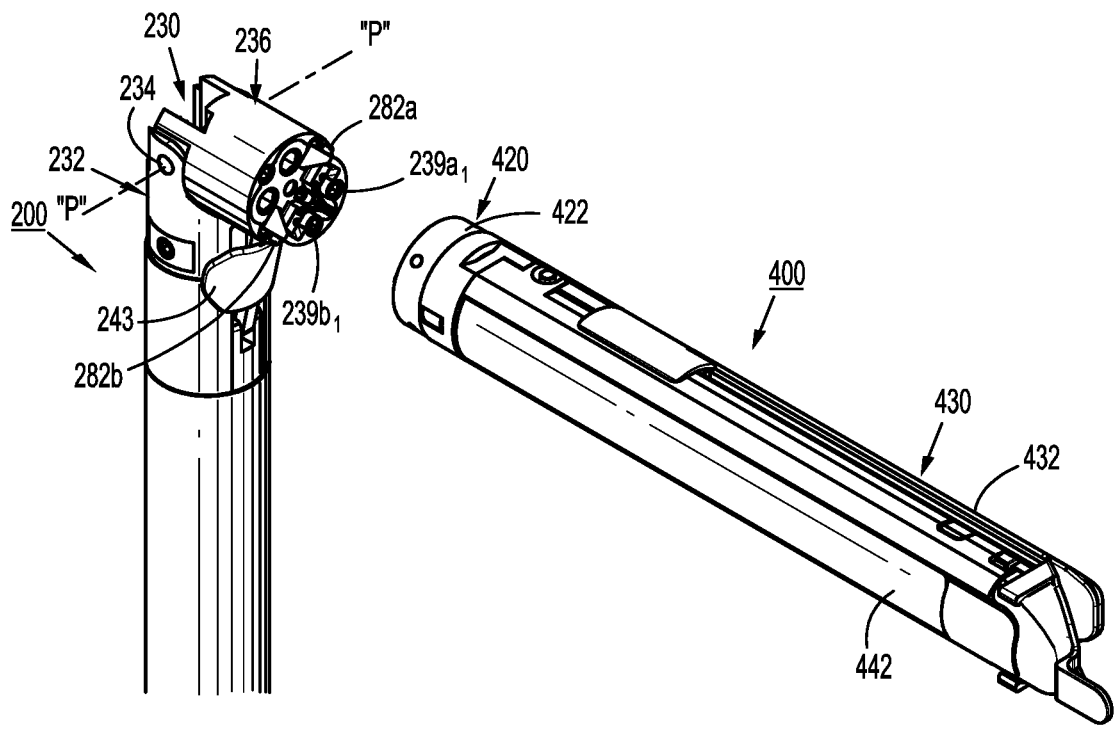
FIG. 24 is a perspective view, illustrating the distal end of the shaft assembly in an articulated condition and the end effector being connected thereto while in a second angular orientation.

Proximal neck housing 232 defines a chamfered distal surface 232a, and distal neck housing 236 defines a chamfered proximal surface 236a. In an embodiment, chamfered surfaces 232a, 236a are in juxtaposed relation to one another. In use, when end effector 400 is actuated to an off-axis orientation, as will be discussed in greater detail below, chamfered surfaces 232a, 236a of proximal neck housing 232 and distal neck housing 236 are approximated toward one another. Desirably, each chamfered surface 232a, 236a is angled at about 45° relative to the longitudinal axis "X". Specifically, chamfered surface 232a of proximal neck housing 232 is angled at about (−)45° relative to the longitudinal axis "X", while chamfered surface 236a of distal neck housing 236 is angled at about (+)45° relative to the longitudinal axis "X". In this manner, when end effector 400 is actuated to a maximum off-axis orientation, as seen in FIGS. 17, 23 and 24, end effector 400 is oriented at about 90° relative to the longitudinal axis "X". In use, end effector 400 may be oriented at any angular orientation from about 0° to about 90° relative to the longitudinal axis "X", as needed or desired, such as, for example, about 45°.

In accordance with the present disclosure, distal neck housing 236 is pivotable in a single direction relative to proximal neck housing 232.

As seen in FIGS. 4-6 and 9, articulating neck assembly 230 includes a shield 243 secured to articulation link 240. Shield 243 functions to protect the user and patient from gear train 238.

Figure 17A:
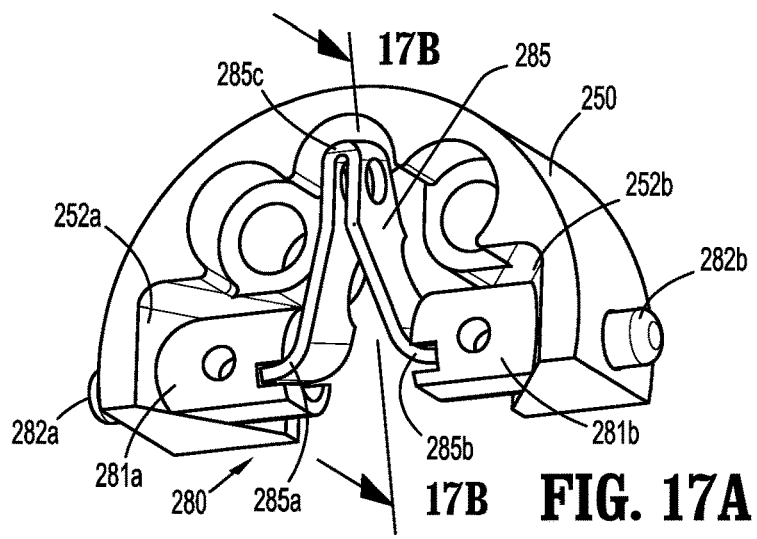
FIGS. 17A-17C are perspective views (with FIG. 17B being a cross-sectional perspective view taken along 17B-17B of FIG. 17A), illustrating an actuation of the release assembly from a locking position to a release position.
Figure 17B:
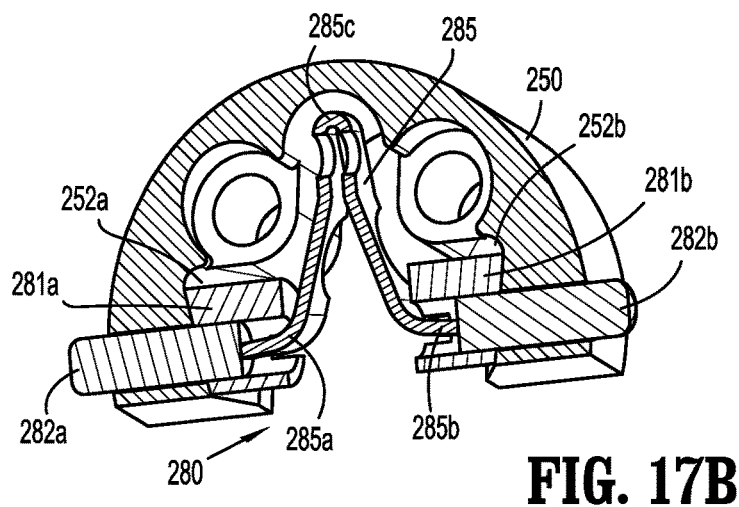
Figure 17C:
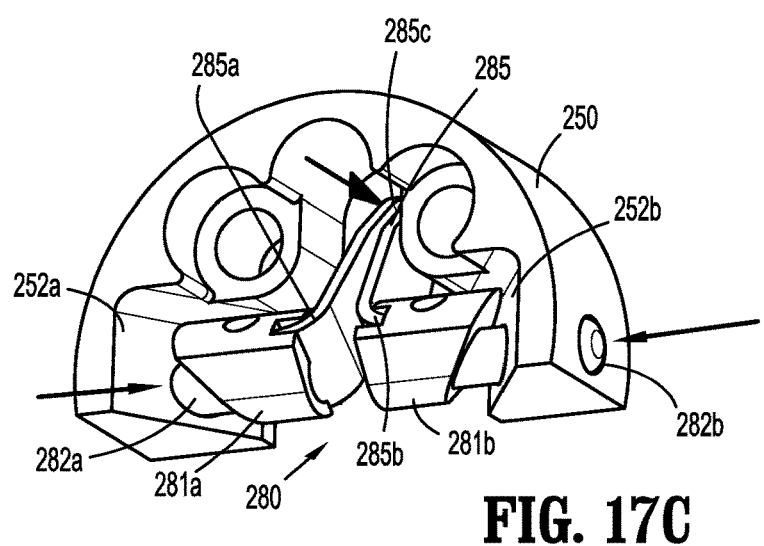

Articulating neck assembly 230 further includes, as seen in FIGS. 5, 6, 9, 10A and 17A-17C, a distal connection hub 250 supported and/or coupled in a distal end of distal neck housing 236. Connection hub 250 rotatably supports both output gears 239a, 239b. In an embodiment, as seen in FIGS. 17A-17C, connection hub 250 defines a pair of diametrically opposed angled surfaces 252a, 252b. Each angled surface 252a, 252b extends in a radially outward direction and in a transverse distal direction relative to a central axis of shaft assembly 200.

Shaft assembly 200, as seen in FIGS. 4-8, 10A-10D and 14-17C, includes a release assembly 280 at least partially supported in/on connection hub 250. Release assembly 280 includes a pair of cam blocks 281a, 281b, each operatively associated with a respective angled surface 252a, 252b of connection hub 250. Release assembly 280 further includes a pair of connection pins 282a, 282b, each connected to and secured to respective cam blocks 281a, 281b. Each connection pin 282a, 282b is dimensioned to extend from respective cam block 281a, 281b and radially through connection hub 250. Specifically, each connection pin 282a, 282b includes a tip which projects radially outward from connection hub 250, when release assembly 280 is in a non-actuated condition.

Release assembly 280 further includes a release lever 285 in the form of a leaf spring defining a biasing member interposed between cam blocks 281a, 281b and functioning to maintain or urge cam blocks 281a, 281b into engagement or contact with respective angled surface 252a, 252b of connection hub 250. Release lever 285 includes a pair of ends 285a, 285b secured to a respective cam block 281a, 281b, and a free end 285c projecting radially from the axis defined by connection pins 282a, 282b.

Release assembly 280 includes a first or connecting configuration wherein a tip of each connection pin 282a, 282b projects radially outward from connection hub 250, and a second or release configuration wherein the tip of each connection pin 282a, 282b is at least partially withdrawn or retracted into connection hub 250.

In use, as seen in FIGS. 17A-17C, in order to actuate release assembly 280 from the first configuration to the second configuration, release lever 285 is actuated to rotate release lever 285 about the axis defined by connection pins 282a, 282b. As release lever 285 is actuated, cam blocks 281a, 281b are rotated relative to respective angled surface 252a, 252b of connection hub 250 thereby urging respective connection pins 282a, 282b radially inward, and biasing or compressing the leaf spring portion of release lever 285. Following actuation of release lever 285, upon a release thereof, the leafspring un-compresses and urges cam blocks 281a, 281b against respective angled surface 252a, 252b of connection hub 250 causing cam blocks 281a, 281b to return to an un-rotated position and resulting in connection pins 282a, 282b re-extending radially outward from connection hub 250.

Figure 10A:
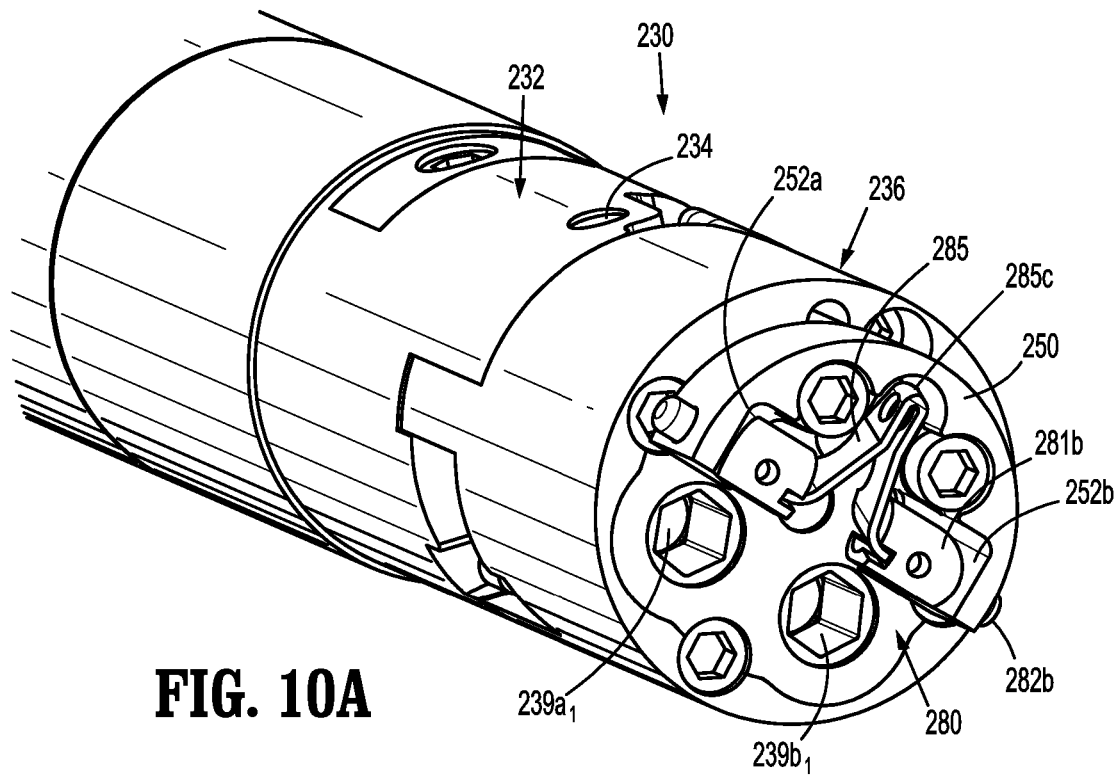
FIG. 10A is an enlarged, front, perspective view of the shaft assembly of FIGS. 1 and 3-9, illustrating a release assembly thereof.
Figure 10B:
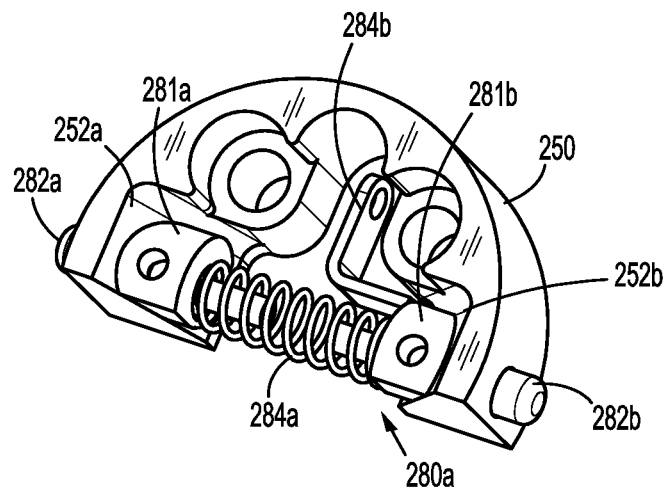
FIG. 10 B is a perspective view of a release assembly according to another embodiment of the present disclosure.
FIG. 10C is another perspective view of the release assembly of FIG. 10A.
FIG. 10D is a perspective view of a release assembly according to yet another embodiment of the present disclosure.
Figure 10C:
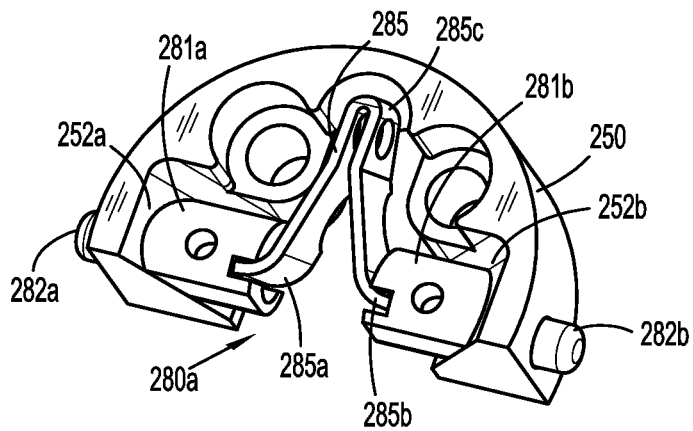

In an alternate embodiment of a release assembly 280a, as seen in FIG. 10B, leaf spring release lever 285 of release assembly 280 may be replaced with a separate biasing member 284a and release lever 284b.

Release assembly 280 also includes a release lever 285 connected to at least one cam block 281a, 281b. In the present embodiment, release lever 285 extends in a direction transverse to an axis defined by connection pins 282a, 282b.

Figure 10D:
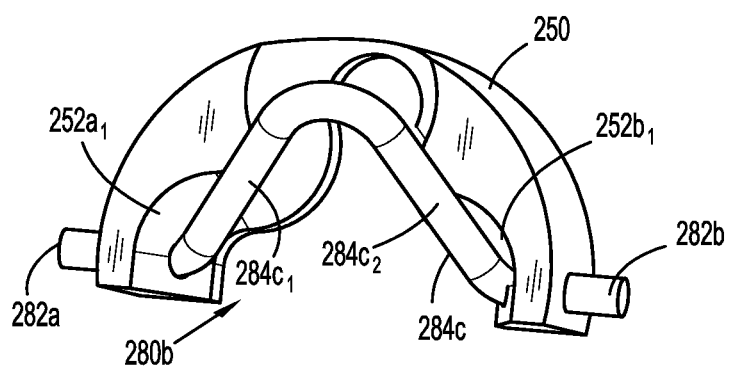
Figure 16A:
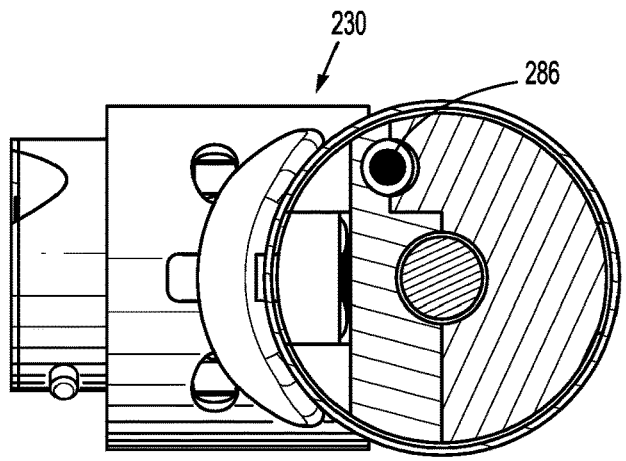
FIG. 16A is a cross-sectional view as taken and viewed along 16A-16A of FIG. 16.

In yet another alternate embodiment, as seen in FIG. 10D, another alternate release assembly 280b may include a resilient wire-like release lever 284c including a pair of arms $284c_1$, $284c_2$ arranged in a substantial V-shape or a-shape, and a pair of connection pins $282a_1$, $282b_1$ extending from a respective arm $284c_1$, $284c_2$. Release lever 284c of release assembly 280b cooperates with particularly shaped camming surfaces $252a_1$, $252b_1$ of connection hub 250.

In use, in order to actuate release assembly 280b from a first configuration to a second configuration, release lever 284c is actuated to rotate arms $284c_1$, $284c_2$ about an axis defined by connection pins $282a_1$, $282b_1$. As release lever 284c is actuated, arms $284c_1$, $284c_2$ engage respective angled surfaces $252a_1$, $252b_1$ of connection hub 250 thereby urging respective arms $284c_1$, $284c_2$ and thus connection pins $282a_1$, $282b_1$ radially inward, and biasing or compressing arms $284c_1$, $284c_2$ toward one another. Following actuation of release lever 284c, upon a release thereof, arms $284c_1$, $284c_2$ un-compress and urge connection pins $282a_1$, $282b_1$ radially outward from connection hub 250.

Turning now to FIGS. 14-17, release assembly 280 includes a release cable 286 extending through articulation neck assembly 230 and tubular body 210 of shaft assembly 200. Specifically, release cable 286 includes a distal end connected to a free end 285c of release lever 285. Release cable 286 also includes a proximal end connected to a release button 287 which is slidably supported on transmission housing 208. Release button 287 includes a first position wherein release assembly 280 is un-actuated, as described above, and at least a second position wherein release button 287 pulls release cable 286 in a proximal direction to actuate release assembly 280.

Release assembly 280 further includes a slack removal assembly 288 including a spring 288a, or the like, associated with release cable 286. Slack removal spring 288a functions to compensate for any slack or stretching that may occur in release cable 286 over time and after any number of uses, or when articulation neck assembly 230 is in an articulate configuration. In particular, slack removal assembly 288 further includes a cylinder 288b into which a proximal end of release cable 286 extends. Release button 287 is connected to cylinder 288b such that axial movement of release button 287 results in concomitant axial movement of cylinder 288b. Slack removal spring 288a is supported in cylinder 288b. The proximal end of release cable 286 extends through slack removal spring 288a and is capped by a plug 288c fixedly connected thereto. Desirably, slack removal spring 288a is a coil spring or the like.

As seen in FIGS. 3 and 8, shaft assembly 200 includes a pair of electrical contact pins 290a, 290b for electrical connection to a corresponding electrical plug 190a, 190b disposed in connecting portion 108a of surgical device 100. Electrical contacts 290a, 290b serve to allow for calibration and communication of necessary life-cycle information to circuit board of surgical device 100 via electrical plugs 190a, 190b that are electrically connected to circuit board. Shaft assembly 200 further includes a circuit board 292 supported in transmission housing 208 and which is in electrical communication with electrical contact pins 290a, 290b. In accordance with the present disclosure, shaft assembly 200 or circuit board 292 include a button 294 (see FIGS. 7 and 8), which functions in the manner of a gyroscope, Hall-Effect sensors or the like, to communicate with surgical device 100 and provide surgical device 100 with an indication of when shaft assembly is not rotated (i.e., in a home or straight position or configuration). In this manner, button 294 functions to inhibit instances of excessive rotation of shaft assembly 200.

Turning now to FIGS. 18-24, a detailed discussion of the construction and operation of end effector 400 is provided. End effector 400 is constructed substantially in accordance with end effector 400 disclosed in U.S. patent application Ser. No. 13/891,288, filed on May 10, 2013, now U.S. Pat. No. 9,492,146, the entire content of which being incorporated herein by reference, and thus will only be discussed in detail herein to the extent necessary to describe differences in construction and operation thereof. End effector 400 may be configured and adapted to apply a plurality of linear rows of fasteners, which in embodiments may be of various sizes, and which, in certain embodiments may have various lengths or rows, e.g., about 30, 45 and 60 mm in length.

As seen in FIGS. 1 and 18-24, end effector 400 includes a mounting portion 420 having a coupling member 422 configured for selective connection to distal neck housing 236 of shaft assembly 200. End effector 400 further includes a jaw assembly 430 connected to and extending distally from mounting portion 420. Jaw assembly 430 includes a lower jaw 432 pivotally connected to mounting portion 420 and being configured to selectively support a cartridge assembly therein, and an upper jaw 442 secured to mounting portion 420 and being movable, relative to lower jaw 432, between approximated and spaced apart positions.

Figure 20:
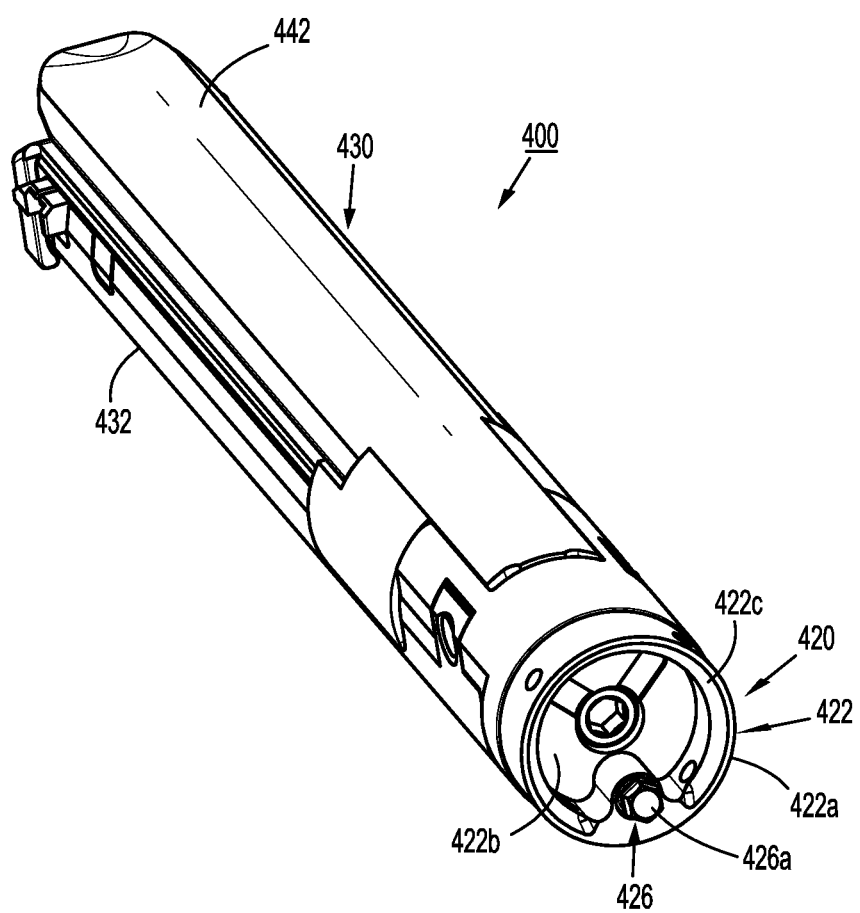
FIG. 20 is a rear, perspective view of the end effector of FIG. 18.

As seen in FIGS. 20 and 21, coupling member 422 is substantially cylindrical and includes a rear or proximal annular wall 422a defining a central opening 422b therein. Annular wall 422a defines an angled inner surface 422c extending radially inwardly and distally from a proximal-most edge. Annular wall 422a further defines two pair of diametrically opposed attachment holes 422d1, 422$d_2$ oriented orthogonally to one another. Central opening 422b is configured and dimensioned to receive connection hub 250 of shaft assembly 200 therein.

In use, when end effector 400 is connected to attached to shaft assembly 200, end effector 400 is oriented in either a first orientation, or a second orientation rotated approximately 90°, along a longitudinal axis thereof, relative to the first orientation.

As seen in FIG. 21 and FIG. 23, in the first orientation, attachment holes 422d1 are aligned with connection pins 282a, 282b of release assembly 280 of shaft assembly, and a proximal head 426a of a drive axle 426 of end effector 400 is aligned with coupling socket 239$a_1$. As so oriented, end effector 400 is approximated toward shaft assembly 200 wherein connection pins 282a, 282b of release assembly 280 are cammed radially inwardly as connection pins 282a, 282b engage angled inner surface 422c of coupling member until connection pins 282a, 282b align with attachment holes 422d1 whereby connection pins 282a, 282b are free to spring radially outward into attachment holes 422d1 to secure end effector 400 to shaft assembly 200. Also, as so oriented, when end effector 400 is connected to shaft assembly 200, proximal head 426a of drive axle 426 of end effector 400 operatively couples with coupling socket 239$a_1$.

In this first orientation, as seen in FIG. 23, a plane defined between tissue contacting surfaces of upper jaw 442 and lower jaw 432 of jaw assembly 430 is substantially parallel to the pivot axis "P" defined by pivot pin 234.

As seen in FIGS. 21 and 24, in the second orientation, attachment holes 422$d_2$ are aligned with connection pins 282a, 282b of release assembly 280 of shaft assembly, and proximal head 426a of drive axle 426 of end effector 400 is aligned with coupling socket 239$b_1$. As so oriented, end effector 400 is approximated toward shaft assembly 200 wherein connection pins 282a, 282b of release assembly 280 are cammed radially inwardly as connection pins 282a, 282b engage angled inner surface 422c of coupling member until connection pins 282a, 282b align with attachment holes 422$d_2$ whereby connection pins 282a, 282b are free to spring radially outward into attachment holes 422$d_2$ to secure end effector 400 to shaft assembly 200. Also, as so oriented, when end effector 400 is connected to shaft assembly 200, proximal head 426a of drive axle 426 of end effector 400 operatively couples with coupling socket 239$b_1$.

In this second orientation, as seen in FIG. 24, a plane defined between tissue contacting surfaces of upper jaw 442 and lower jaw 432 of jaw assembly 430 is substantially orthogonal to the pivot axis "P" defined by pivot pin 234.

As seen in FIG. 19, lower jaw 432 of jaw assembly 430 includes a drive screw 464 rotatably supported therein and extending substantially an entire length thereof. Drive screw 464 includes a female coupling member 464a supported on a proximal end thereof and being configured for receipt of multi-faceted, distal head 426b of drive axle 426. Drive screw 464 is axially and laterally fixed within lower jaw 432 of jaw assembly 430. In operation, rotation of drive axle 426 results in concomitant rotation of drive screw 464.

End effector 400 includes a drive beam 466 slidably supported in lower jaw 432 of jaw assembly 430. Drive beam 466 includes a substantially I-shaped cross-sectional profile and is configured to approximate lower jaw 432 and upper jaw 442, and to axially displace an actuation sled 418 through lower jaw 432. Drive beam 466 includes a vertically oriented support strut; a lateral projecting member formed atop the support strut and being configured to engage and translate with respect to an exterior camming surface of upper jaw 442 to progressively close jaw assembly 430; and a retention foot having an internally threaded bore for threadable connection to threaded drive screw 464. Since drive beam 466 is prevented from rotation by the engagement of the strut and/or the cam member with upper jaw 442, as drive screw 464 is rotated, the retention foot, and in turn, drive beam 466 is axially translated relative to lower jaw 432.

In operation, as drive screw 464 is rotated, in a first direction, to advance drive beam 466, as described above, drive beam 466 is advanced into contact with a knife sled 450 and an actuation sled 418 to distally advance or push knife sled 450 and actuation sled 418 through staple cartridge assembly 410 and lower jaw 432. Knife sled 450, actuation sled 418 and drive beam 466 travel through a body of cartridge assembly 410 thereby fastening and severing tissue. Drive screw 464 is rotated until actuation sled 418, knife sled 450 and drive beam 466 reach a distal-most end of the body of cartridge assembly 410 and/or lower jaw 432, for a complete firing.

Following a complete or partial firing, drive screw 464 is rotated in an opposite direction to retract drive beam 466. Drive screw 464 is rotated until drive beam 466 and knife sled 450 are returned to the proximal-most position. Once drive beam 466 and knife sled 450 are returned to the proximal-most position, drive beam 466 is disengaged from knife sled 450, and staple cartridge assembly 410 is free to be removed from lower jaw 432.

Upper jaw 442 of jaw assembly 430 functions as an anvil against which the staples form when actuation sled 418 is advanced during a firing of surgical device 100. In particular, upper jaw 442 includes an anvil plate 443, secured to a cover housing 444, in juxtaposed relation to staple cartridge assembly 410. Anvil plate 443 defines a plurality of staple forming pockets (not shown), arranged in longitudinally extending rows that cooperate with the rows of staple retaining slots (not shown) of staple cartridge assembly 410, when staple cartridge assembly 410 is disposed in lower jaw 432.

It will be understood that various modifications may be made to the embodiments disclosed herein. For example, surgical device 100 and/or cartridge assembly 410 need not apply staples but rather may apply two part fasteners as is known in the art. Further, the length of the linear row of staples or fasteners may be modified to meet the requirements of a particular surgical procedure. Thus, the length of the linear row of staples and/or fasteners within a staple cartridge assembly may be varied accordingly. Therefore, the above description should not be construed as limiting, but merely as exemplifications of preferred embodiments. Those skilled in the art will envision other modifications within the scope and spirit of the claims appended thereto.

What is claimed:

1. A release assembly for selectively interconnecting an end effector and a shaft assembly of a surgical instrument, the release assembly comprising:

a lever including a first arm, a second arm, a first pin extending from the first arm, and a second pin extending from the second arm, the first pin defining a rotational axis transverse to a longitudinal axis of the shaft assembly, a portion of the lever being rotatable about the rotational axis.

2. The release assembly according to claim 1, wherein the first arm and the second arm of the lever are rotatable about the rotational axis.

3. The release assembly according to claim 1, wherein the first arm and the second arm of the lever are arranged in a substantial V-shape.

4. The release assembly according to claim 1, wherein the second pin is disposed along the rotational axis.

5. The release assembly according to claim 1, further comprising a connection hub disposed in mechanical cooperation with the lever.

6. The release assembly according to claim 5, wherein the first pin of the lever extends through an opening defined in the connection hub.

7. The release assembly according to claim 5, wherein the connection hub includes a first camming surface configured for selective engagement with the first arm of the lever.

8. The release assembly according to claim 7, wherein the connection hub includes a second camming surface configured for selective engagement with the second arm of the lever.

9. The release assembly according to claim 1, further comprising a release button and a release cable, the release cable interconnecting the release button and the first pin of the lever.

10. A release assembly for selectively interconnecting an end effector and a shaft assembly of a surgical instrument, the release assembly comprising:
a lever including a first pin and a second pin, the first pin defining a rotational axis transverse to a longitudinal axis of the shaft assembly, the second pin being disposed along the rotational axis, a portion of the lever being rotatable about the rotational axis.

11. The release assembly according to claim 10, further comprising a connection hub disposed in mechanical cooperation with the lever.

12. The release assembly according to claim 11, wherein the first pin of the lever extends through an opening defined in the connection hub.

13. The release assembly according to claim 11, wherein the lever includes a first arm and a second arm, and wherein the connection hub includes a first camming surface configured for selective engagement with the first arm of the lever.

14. The release assembly according to claim 13, wherein the connection hub includes a second camming surface configured for selective engagement with the second arm of the lever.

15. The release assembly according to claim 10, further comprising a release button and a release cable, the release cable interconnecting the release button and the first pin of the lever.

16. A release assembly for selectively interconnecting an end effector and a shaft assembly of a surgical instrument, the release assembly comprising:
a lever including a first pin and a second pin, the first pin defining a rotational axis transverse to a longitudinal axis of the shaft assembly, a portion of the lever being rotatable about the rotational axis; and
a release button and a release cable, the release cable interconnecting the release button and the first pin of the lever.

17. The release assembly according to claim 16, further comprising a connection hub disposed in mechanical cooperation with the lever.

18. The release assembly according to claim 17, wherein the first pin of the lever extends through an opening defined in the connection hub.

19. The release assembly according to claim 17, wherein the lever includes a first arm and a second arm, and wherein the connection hub includes a first camming surface configured for selective engagement with the first arm of the lever.

20. The release assembly according to claim 19, wherein the connection hub includes a second camming surface configured for selective engagement with the second arm of the lever.

* * * * *